US012023103B2

(12) United States Patent
Roh et al.

(10) Patent No.: US 12,023,103 B2
(45) Date of Patent: Jul. 2, 2024

(54) 3D PRINTING OF STRUCTURES INSIDE A PATIENT

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael J. Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/895,281

(22) Filed: Aug. 25, 2022

(65) Prior Publication Data
US 2024/0065762 A1 Feb. 29, 2024

(51) Int. Cl.
A61B 34/10 (2016.01)
A61F 2/30 (2006.01)

(52) U.S. Cl.
CPC ............ *A61B 34/10* (2016.02); *A61F 2/3094* (2013.01); *A61B 2034/105* (2016.02)

(58) Field of Classification Search
None
See application file for complete search history.

(56) References Cited

U.S. PATENT DOCUMENTS

| 11,337,762 B2 * | 5/2022 | Mckinnon | G16H 50/50 |
| 11,523,916 B2 * | 12/2022 | Dewey | A61B 34/30 |
| 2007/0118243 A1 * | 5/2007 | Schroeder | A61F 2/2875 |
| | | | 700/98 |
| 2016/0231732 A1 * | 8/2016 | Neetz | G16H 30/20 |
| 2020/0101273 A1 * | 4/2020 | Yoo | A61M 35/00 |
| 2021/0177603 A1 * | 6/2021 | Dewey | B33Y 80/00 |
| 2021/0177623 A1 * | 6/2021 | Dewey | A61B 34/30 |
| 2021/0251704 A1 * | 8/2021 | Velis | B22F 12/22 |
| 2023/0107003 A1 * | 4/2023 | Roh | A61B 5/0836 |
| | | | 606/1 |
| 2023/0181256 A1 * | 6/2023 | Roh | A61B 34/10 |
| | | | 703/6 |
| 2023/0298728 A1 * | 9/2023 | Casey | G16H 20/40 |
| | | | 705/3 |
| 2023/0301791 A1 * | 9/2023 | Dean | A61B 34/10 |

(Continued)

FOREIGN PATENT DOCUMENTS

WO WO-2013177051 A1 * 11/2013 ............ A61B 34/10

*Primary Examiner* — Jennifer L Norton
(74) *Attorney, Agent, or Firm* — Fish & Richardson P.C.

(57) ABSTRACT

The disclosed technology provides for printing a 3D structure in-situ within a patient during a surgical procedure. The disclosed technology can include generating instructions for a 3D printer of a surgical robot to print a structure within the patient's body, simulating and verifying the instructions, and autonomously or semi-autonomously executing the instructions, once verified, during a surgical procedure. Generating the instructions for printing the 3D structure within the patient can be based on image data of the patient. Generating the instructions can also include selecting substrate materials that are both safe for the patient and having desired properties of the final printed structure. Modifications can be made to the instructions based on results from the simulation. The disclosed technology provides for application of safe substrate material directly to hard and/or soft tissues within the patient's body via an additive manufacturing process, such as 3D printing.

26 Claims, 12 Drawing Sheets

(56) References Cited

U.S. PATENT DOCUMENTS

| | | | |
|---|---|---|---|
| 2023/0363832 A1* | 11/2023 | Mosadegh | G16H 20/40 |
| 2023/0377714 A1* | 11/2023 | Liarno | G16H 20/40 |
| 2023/0397964 A1* | 12/2023 | Roh | A61B 90/37 |

\* cited by examiner

Patient Database 130

| Patient ID | Age | Gender | Height (in.) | Allergies | Conditions | Image Files |
|---|---|---|---|---|---|---|
| M_0026 | 46 | Male | 70 | None | None | MRI_pelvis_3-20-2022 |
| F_0165 | 36 | Female | 65 | None | None | XRAY_r-knee_2-4-2022 |
| F_0654 | 48 | Female | 68 | Latex | Breast Cancer | CT_chest_1-5-2022 |
| M_0264 | 65 | Male | 72 | None | Coronary Heart Disease | CT_chest_2-16-2022 |
| F_0544 | 72 | Female | 63 | None | Osteoporosis | XRAY_pelvis_2-25-2022 |

FIG. 2

Procedure Database 132

| Procedure ID | Patient ID | Surgeon ID | Procedure |
|---|---|---|---|
| 465463 | M_0026 | 1654 | Pelvis reconstruction |
| 847324 | F_0165 | 1548 | Knee replacement |
| 321698 | F_0654 | 1265 | Masectomy and breast reconstruction |
| 765864 | M_0264 | 1874 | Triple bypass |
| 679465 | F_0544 | 1324 | Hip fracture repair |

FIG. 3

Substrate Database 134

| Substrate ID | Material | Material Type | Extrusion Method | Curing Method |
|---|---|---|---|---|
| 135 | UV Curable Resin | Resin | Pumped Gel | Ultraviolet Light |
| 136 | Alumina | Compound | Extruded Paste | Laser Sintering |
| 137 | Cobalt-chromium Alloy | Metal Alloy | Extruded Paste | Laser Sintering |
| 138 | Medical-grade Silicone | Resin | Pumped Gel | Two Part Cure |
| 139 | Polyvinylchloride | Thermoplastic | Extruded Melted Plastic | Cooling |
| 140 | Polyethylene | Thermoplastic | Extruded Melted Plastic | Cooling |
| 141 | Polypropylene | Thermoplastic | Extruded Melted Plastic | Cooling |
| 142 | Stainless Steel | Metal | Powder in Binder | Laser Sintering |
| 143 | Titanium | Metal | Powder in Binder | Laser Sintering |
| 144 | Ziconia | Ceramic | Powder in Binder | Laser Sintering |

FIG. 4

3D PRINTING OF STRUCTURES INSIDE A PATIENT

TECHNICAL FIELD

This document describes devices, systems, and methods related to medical implants, particularly 3D printing of customized medical implants inside, adjacent, affixed to, or otherwise around one or more anatomical structures of a patient's body.

BACKGROUND

Some patients may require procedures in which medical implants are inserted inside a patient's body. A procedure can be performed in which a surgeon or other medical practitioner inserts an implant inside the patient's body to provide therapeutic and/or diagnostic benefits before, during, and/or after the procedure. The surgeon can manually insert the implant inside the patient. The surgeon can also use robotic systems to assist in accurately and safely inserting the implant inside the patient. Such robotic systems can relieve the surgeon from performing some routine tasks while also making the procedure safe and less costly for the patient. The robotic systems can also aid in performing accurate procedures in small locations in the patient's body that may be challenging to precisely target by a human.

Some implants can be installed as one piece while other implants can be installed in situ as an assembly of components. The assembly of components may be expandable, such that they may be inserted, manually by the surgeon and/or by the robotic systems, through a smaller space than their functional dimension and then expanded to their final functional dimension after they have been navigated to their destination inside the patient. Such methods of installing implants can have non-negligible dimensional sizes that can make installing the implants using minimally invasive techniques challenging.

SUMMARY

The document generally relates to technology for in situ 3D printing of an implant or other structure inside, adjacent, affixed to, or otherwise around one or more anatomical structures of a patient's body during a procedure. Although the disclosed technology is described in reference to 3D printing, one or more other additive manufacturing techniques and processes can also be used to generate an implant or other structure directly within the patient's body during the procedure. A patient may require an implant inserted inside their body for therapeutic and/or other health benefits. Using the disclosed technology, instructions for 3D printing the implant at a desired location inside the patient's body can be generated. The 3D instructions for printing the implant inside the patient's body can also be simulated before the implant procedure to improve accuracy of the 3D printing instructions and ensure patient safety and health will be maintained during runtime execution of the 3D printing during the implant procedure. The 3D printing instructions can be refined based on the simulation results. Then, the 3D printing instructions can be executed during runtime so that the implant can be safely and precisely 3D printed at the desired location inside the patient's body. The 3D printing instructions can be executed by a surgical robotic system, such as a robotic arm. The robotic system can be controlled or manipulated by a surgeon or other medical professional. In some implementations, the robotic system can also be autonomous or semi-autonomous and can receive instructions for executing the 3D printing instructions from a computer system.

Installing implants using minimally invasive techniques can have complications related to the dimensions of implant components. For example, angles and other physical features of the implant components may cause the implant to get caught on soft and/or hard tissues inside the patient. This can complicate a procedure by adding time and increasing a skill level of a surgeon or robotic system needed to navigate the implant components inside the patient without causing damage to the patient.

Sometimes, an implant can be customized for a particular patient. Customizing the implant can be expensive. Customizing the implant can also result in long wait times for the implant to be manufactured, which can delay a much-needed procedure for the patient. Additionally, some custom implants may be limited in that they must be insertable into the patient's body and sometimes may require modification of the patient's body, such as removing tissue, to accommodate the implant.

One or more embodiments described herein can include a method for printing a structure in situ within a patient's body, the method including: receiving, by a computer system, image data of a print site within a patient's body, the print site indicating a location at least partially inside the patient's body on which a structure is to be printed, identifying, by the computer system and based on the received image data, a print surface of the print site within the patient's body, generating, by the computer system, printing instructions for printing the structure on the identified print surface at the print site within the patient's body, and controlling, by the computer system, a printing device to physically print the structure at the print site at least partially inside the patient's body using the printing instructions.

In some implementations, the embodiments described herein can optionally include one or more of the following features. For example, generating the printing instructions can include: simulating, by the computer system, the printing instructions using the received image data, to verify successful printing of the structure at least partially inside the patient's body, determining, by the computer system, whether simulating the printing instructions is successful, and generating, by the computer system and based on a determination that the simulation is successful, the printing instructions to be executed by a controller of a surgical robot having the printing device to print the structure at the print site at least partially inside the patient's body during the surgical procedure and using the printing instructions.

In some implementations, the printing device can be a 3D printer. The printing device can be an additive manufacturing device. The structure can be an implant. Receiving, by the computer system, the image data can be performed by a base module of the computer system. Generating, by the computer system, the printing instructions can be performed by a planning module of the computer system. Simulating, by the computer system, the printing instructions can be performed by a simulation module of the computer system. Generating, by the computer system and based on a determination that the simulation is successful, the printing instructions can be performed by a print module of the computer system.

As another example, generating, by the computer system, the printing instructions can include: retrieving procedure data for a surgical procedure to be performed to print the structure at the print site within the patient's body, generating, based on the identified print surface and the retrieved procedure data, a print design for the structure to be printed on the identified print surface at the print site within the patient's body, retrieving substrate material data for substrate materials to be used in printing the structure according to the print design, and selecting at least one of the substrate materials based on respective substrate material data satisfying printing criteria. As another example, the method can also include generating, by the computer system and based on the simulating being unsuccessful, an error report, the error report including indications of issues during simulated execution of one or more of the printing instructions, modifying, by the computer system and based on the error report, the one or more of the printing instructions, and simulating, by the computer system, the modified printing instructions to verify successful printing of the structure at least partially inside the patient's body.

As yet another example, controlling, by the computer system, the printing device to physically print the structure computer system, at the print site at least partially inside the patient's body using the printing instructions can include: generating instructions, based on the printing instructions, that, when executed by the printing device, cause the printing device to apply a substrate material to the prepared print surface, continuously receiving, from at least one imaging device, image data of the print surface as the print surface is prepared and the substrate material is applied to the prepared print surface, determining, based on the received image data, whether the structure is being printed by the printing device according to the printing instructions, and returning, based on a determination that the structure is being printed according to the printing instructions, an indication that the structure is printed at least partially inside the patient's body during the surgical procedure. The method can also include generating instructions, based on the printing instructions, that, when executed by the printing device, cause the printing device to apply an adhesion layer to the prepared print surface before applying the substrate material. The method can also include generating, based on a determination that the structure is not printed according to the printing instructions, instructions that, when executed by the printing device, cause the printing device to stop printing the structure at least partially inside the patient's body, and transmitting the instructions to the printing device for execution during the surgical procedure. In some implementations, the printing instructions may include instructions that cause the printing device to prepare the print surface, the instructions comprising at least one of (i) removing soft tissue near the print surface within the patient's body, (ii) cleaning a bone surface within the patient's body that is part of the print surface, (iii) drying the bone surface within the patient's body that is part of the print surface, (iv) removing a portion of the bone surface, and (v) removing failing internal structures of the patient's body to be replaced by the structure. Moreover, generating instructions, based on the printing instructions, that, when executed by the printing device, cause the printing device to apply the substrate material to the prepared print surface can include: drawing, by an extruder of the printing device, the substrate material from a supply, and depositing, by the extruder via a nozzle of the printing device, a predetermined amount of the drawn substrate material onto the prepared print surface, the extruder being set to a predetermined position and a predetermined orientation defined by the printing instructions.

In some implementations, the printing instructions may include at least one of (i) a design of the structure to be printed on the print surface at least partially inside the patient's body, (ii) at least one substrate material to use for printing the structure, (iii) a location on the print surface to print the structure with the at least one substrate material, (iv) an indication of at least a portion of the print surface that should remain unattached to the structure, (v) tool pathing for the printing device to print the structure on the print surface, (vi) location and orientation information for the printing structure to print the structure on the print surface, and (vii) instructions for extruding the at least one substrate material on the print surface.

One or more embodiments described herein may include a surgical robot for printing a structure in situ within a patient's body, the surgical robot having: at least one robotic arm that can be configured to perform one or more operations during a surgical procedure, a printing device that can be configured to print a structure on a print surface at least partially inside a patient's body during the surgical procedure, a controller that can be configured to execute instructions, during the surgical procedure, that cause (i) the at least one robotic arm to perform the one or more operations and (ii) the printing device to print the structure on the print surface at least partially inside the patient's body, and a communications interface that can be configured to provide communication between components of the surgical robot.

In some implementations, the surgical robot may optionally include one or more of the following features. For example, the at least one robotic arm may include at least one end effector that can be configured to perform the one or more operations. The printing device can be attached to the at least one robotic arm. The printing device can include an extruder and a nozzle, the printing device being configured to: draw, using the extruder and from a supply, a predetermined quantity of at least one substrate material for use in printing the structure on the print surface at least partially inside the patient's body, and deposit, using the nozzle, the drawn quantity of the at least one substrate material onto the print surface at a predetermined position and orientation of the printing device, the predetermined position and orientation of the printing device being defined by the instructions. Sometimes, the supply can be at least one of a reservoir, a spool of filament, and a hopper of raw pellets. The supply can be attached to the surgical robot. The supply can be separate from the surgical robot and fluidically connected to the printing device via a tubing structure attached to a portion of the surgical robot. The communications interface can be configured to provide communication between the components of the surgical robot and a computer system, the computer system being configured to generate the instructions to be executed by the controller.

The devices, system, and techniques described herein may provide one or more of the following advantages. For example, forming an implant directly inside, adjacent, affixed to, or otherwise around one or more anatomical structures of a patient using the disclosed technology reduces the invasiveness of implant procedures. The implant can be directly 3D printed inside the patient's body, which can avoid potential implications or damage to internal structures of the patient when a traditional implant is inserted through an opening into the patient, navigated through and around the internal structures inside the patient's body, and then expanded once in a desired position inside the patient's body. As a result, the in situ 3D printing of the implant can preserve patient safety and internal structures during the procedure.

The disclosed technology also facilitates a level of customization of implants that allows for the implant to be formed inside the patient's bod and based on structures within the particular patient's body. For example, the implant can be formed inside the patient to fill unique cavities and/or voids within a bone of the patient. Therefore, the implant can provide a stronger connection to the patient's body as well as reinforce the patient's physiology without necessarily occupying space outside the structure being reinforced, which may often be the case with traditional reinforcing plates and/or rods.

As another example, directly manufacturing an implant within the patient's body can eliminate delays that may arise if custom implants are to be created, manufactured, and delivered to a physical site where the patient's procedure is to take place. The disclosed technology provides for the patient's implant procedure to be performed accurately and timely to ensure patient safety.

The details of one or more implementations are set forth in the accompanying drawings and the description below. Other features and advantages will be apparent from the description and drawings, and from the claims.

BRIEF DESCRIPTION OF THE DRAWINGS

FIG. 2 illustrates example patient data used for in situ 3D printing implants during a surgical procedure.

FIG. 3 illustrates example procedure data used for in situ 3D printing implants during a surgical procedure.

FIG. 4 illustrates example substrate data used for in situ 3D printing implants during a surgical procedure.

Like reference symbols in the various drawings indicate like elements.

DETAILED DESCRIPTION OF ILLUSTRATIVE EMBODIMENTS

This document generally relates to technology for 3D printing an implant or other structure inside, adjacent, affixed to, or otherwise around anatomical structures of a patient's body during a surgical procedure, such as an implant procedure. Although the disclosed technology is described in reference to 3D printing, one or more other additive manufacturing techniques and processes can also be used to generate an implant or other structure directly within the patient's body during the surgical procedure.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1A:
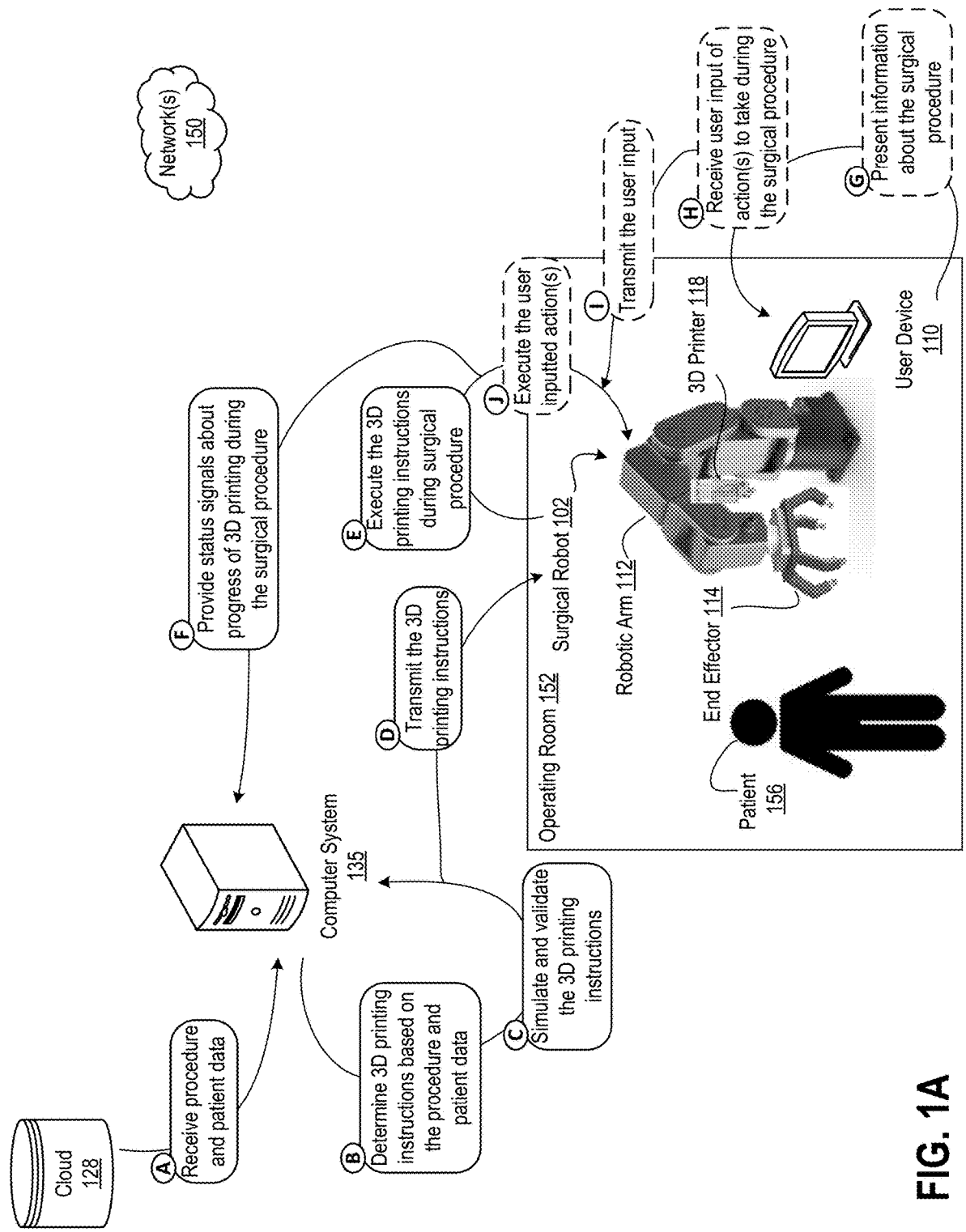
FIG. 1A is a conceptual diagram for performing in situ 3D printing of an implant during a surgical procedure.

Referring to the figures, FIG. 1A is a conceptual diagram for performing in situ 3D printing of an implant during a surgical procedure. A computer system 135 can communicate (e.g., wired and/or wireless) via network(s) 150 with a surgical robot 102, user device 110, and cloud 128. Refer to FIG. 1D for additional discussion about the components 135, 150, 102, 110, and 128. In some implementations, the computer system 135 can be part of the cloud 128. In some implementations, as shown in FIG. 1A, the computer system 135 can be separate from the cloud 128.

The surgical robot 102 can be in an operating room 152 in which the surgical procedure is to be performed on a patient 156. The procedure can include installing an implant or other structure inside, adjacent, affixed to, or otherwise around one or more anatomical structures of the patient 156 to provide health and/or therapeutic benefits. The surgical robot 102 can autonomously or semi-autonomously perform one or more operations during the surgical procedure, as described herein. The surgical robot 102 can include one or more components, such as a robotic arm 112, an end effector 114, and a 3D printer 118. The surgical robot 102 can include one or more additional or fewer components, as described in reference to FIG. 1D. Refer to FIG. 1D for additional discussion about the surgical robot 102.

The user device 110 can be used by a surgeon or other relevant medical professional to view, monitor, and/or control operation of the surgical robot 102 in performing the surgical procedure. Although the user device 110 is shown as being located in the operating room 152 with the surgical robot 102 and the patient 156, in some implementations, the user device 110 can also be physically remote from the operating room 152. Therefore, the surgeon overseeing and/or performing the surgical procedure with the surgical robot 102 can be physically remote from the operating room 152 where the surgical procedure is taking place. The user device 110 can also be referred to as the user interface 110, as depicted and described in reference to FIG. 1D. Moreover, the user device 110 can be part of the surgical robot 102. In some implementations, the user device 110 can be separate from the surgical robot 102. In some implementations, the user device 110 can be part of the computer system 135.

Still referring to FIG. 1A, the computer system 135 can receive procedure and/or patient data in block A from the cloud 128. The data can include image data of the patient 156's body and more specifically, a print site that is inside or otherwise part of the patient 156's body where the implant or other structure is to be printed by the 3D printer 118. The received data can also include information about the procedure to be performed for generating and inserting the implant, information about substrate materials that can be used for printing the implant inside, adjacent, affixed to, or otherwise around the patient 156's body, and/or health information about the patient 156.

The computer system 135 can determine 3D printing instructions (or other additive manufacturing instructions) based on the received procedure and patient data (block B). Refer to processes 500 and 600 in FIGS. 5 and 6 for further discussion about determining the 3D printing instructions.

In block C, the computer system 135 can simulate and validate the 3D printing instructions. If the instructions are not validating during simulation (e.g., one or more issues arise during the simulation), then the computer system 135 can return to block B and modify the instructions. The computer system 135 can continue to simulate the instructions until one or more issues are resolved. Refer to process 700 in FIG. 7 for further discussion about simulating the 3D printing instructions.

Once the instructions are validated, the computer system 135 can transmit the 3D printing instructions to the surgical robot 102 for runtime execution (block D). Accordingly, during the procedure, the surgical robot 102 can execute the 3D printing instructions (block E). Executing the instructions can include using the end effector 114 to prepare the print surface/site for the procedure. Execution can also include using the 3D printer 118 to apply one or more layers of the substrate material at the print surface/site that is inside and/or part of the patient 156's body. Executing the instructions can also include continuously monitoring progress of printing the implant inside, adjacent, affixed to, or otherwise around the patient 156's body using sensor and/or image data received from sensors and/or imaging devices in the operation room 152. Refer to process 800 in FIG. 8 for further discussion about executing the instructions during the surgical procedure to print the implant or other structure inside the patient 156's body.

The surgical robot 102 can also provide one or more status signals about progress of the printing during the surgical procedure to the computer system 135 (block F). The computer system 135 can use the status signal(s) to determine whether the implant is being accurately and precisely printing inside the patient 156's body according to the 3D printing instructions. The computer system 135 can also use the status signal(s) to determine whether the patient 156's health and/or safety is being maintained during the surgical procedure. The computer system 135 can determine one or more modifications/interventions/adjustments to the execution of the printing instructions by the surgical robot 102 based on the status signal(s). Any such modifications, interventions, and/or adjustments can be autonomously executed by the surgical robot 102, semi-autonomously executed by the surgical robot 102, and/or presented to the surgeon at the user device 110 for approval and/or manual implementation.

The user device 110 can optionally present information about the surgical procedure in block G. For example, the status signals generated by the surgical robot 102 can be presented at the user device 110. The computer system 135 can also generate the information about the surgical procedure to be presented at the user device 110. The surgeon can review the information presented at the user device 110 to monitor the procedure and/or the patient 156's conditions.

The user device 110 can optionally receive user input to take one or more actions during the surgical procedure (block H). For example, the surgeon can desire implementing a manual intervention during the procedure to preserve the patient 156's health and/or safety. The surgeon can also desire to semi-autonomously control components of the surgical robot 102 to perform one or more actions during the procedure that are part of (or not part of) the instructions executed by the surgical robot 102 in block E.

The user input can be optionally transmitted from the user device 110 to the surgical robot 102 in block I. The surgical robot 102 can optionally execute the user inputted action(s) during the surgical procedure in block J. The surgical robot 102 can then continue to receive data about the status of the procedure, which can be transmitted to the computer system 135 (block F) and/or the user device 110 throughout the procedure. As described herein, based on the status signals, the computer system 135 can generate one or more interventions to be performed autonomously by the surgical robot 102, semi-autonomously by the surgical robot 102, and/or manually by the surgeon. Refer to FIGS. 5-8 for further discussion about blocks A-J.

Figure 1B:
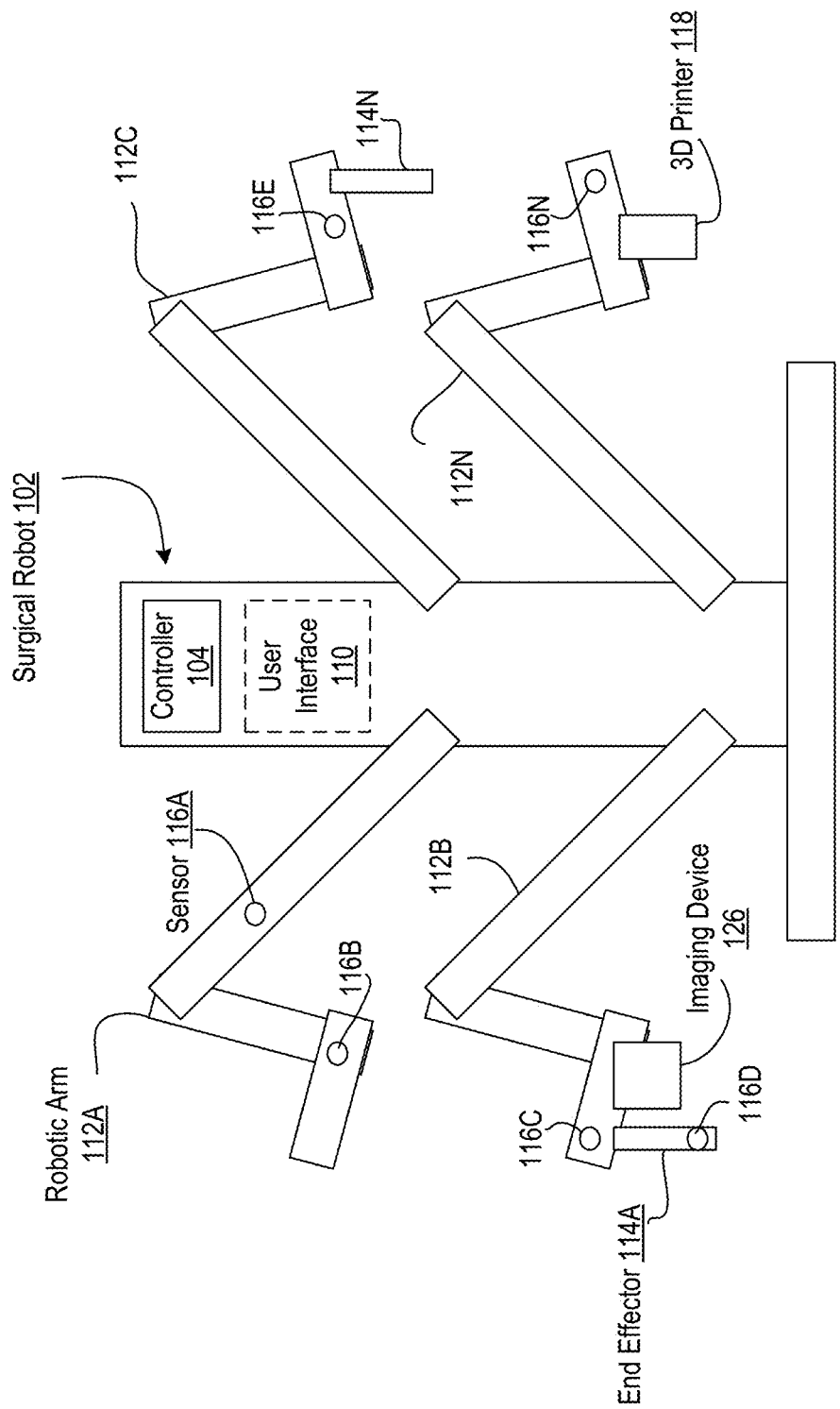
FIG. 1B is an example surgical robot for performing in situ 3D printing of an implant during a surgical procedure.

FIG. 1B is an example surgical robot 102 for performing in situ 3D printing of an implant during a surgical procedure. The surgical robot 102 can include the controller 104 and an optional user interface 110. The surgical robot 102 can include one or more additional or fewer components, as described further in reference to FIG. 1D.

The example surgical robot 102 of FIG. 1B has multiple robot arms 112A-N. In some implementations, the surgical robot 102 can have one robotic arm 112. In some implementations, as shown in FIG. 1B, the surgical robot 102 can have more than one robotic arm 112A-N. Each of the robotic arms 112A-N can be controlled, by the controlled 104, to perform one or more different instructions before, during, and/or after a surgical procedure. Moreover, each of the robotic arms 112A-N can be configured to move in various positions, orientations, angles, rotations, and/or speeds. Each of the robotic arms 112A-N can also be independently controlled by the controller 104 of the surgical robot 102.

Each of the robotic arms 112A-N can include one or more additional tools and/or components for performing the one or more instructions of the surgical procedure. As an illustrative example, the robotic arm 112A can include sensors 116A and 116B. The sensors 116A and 116B can be configured to collect data about a patient of the surgical procedure and/or functioning of the components of the surgical robot 102. Data collected by the sensors 116A and 116B can be used to determine one or more instructions and/or modifications to instructions to be performed during the surgical procedure.

As another example, the robotic arm 112B can include sensors 116C-D, end effector 114A, and imaging device 126. The robotic arm 112B can include one or more additional or fewer components. The end effector 114A can be any type of surgical tool used for performing one or more instructions before, during, and/or after the surgical procedure. The imaging device 126 can be configured to image an area of the patient's body, such as a print surface or other print site at least partially or wholly within or inside the patient's body where an implant or other structure is to be 3D printed.

As another example, the robotic arm 112C can include sensor 116E and end effector 114N. The robotic arm 112C can include one or more additional or fewer components. Each of the sensor 116E and/or the end effector 114N can be configured to perform different or same operations as the sensors and/or end effectors of the surgical robot 102.

As another example, the robotic arm 112N can include a sensor 116N and 3D printer 118. Refer to FIG. 1D for additional discussion about the 3D printer 118. The robotic arm 112N can include one or more additional or fewer components, as described herein.

In some implementations, the 3D printer 118 can be separate from any of the robotic arms 112A-N. The 3D printer 118 can be part of the surgical robot 102. The 3D printer 118 can also be separate from the surgical robot 102 and one or more components of the 3D printer 118 (e.g., a nozzle for depositing substrate material to form a structure inside, affixed to, adjacent, or otherwise adjacent one or more anatomical structures or locations of the patient's body) can be fluidically connected to the surgical robot 102, such as being fluidically connected to one or more of the end effectors 114A-N. One or more other configurations of the surgical robot 102 of FIG. 1B are also possible.

Figure 1C:
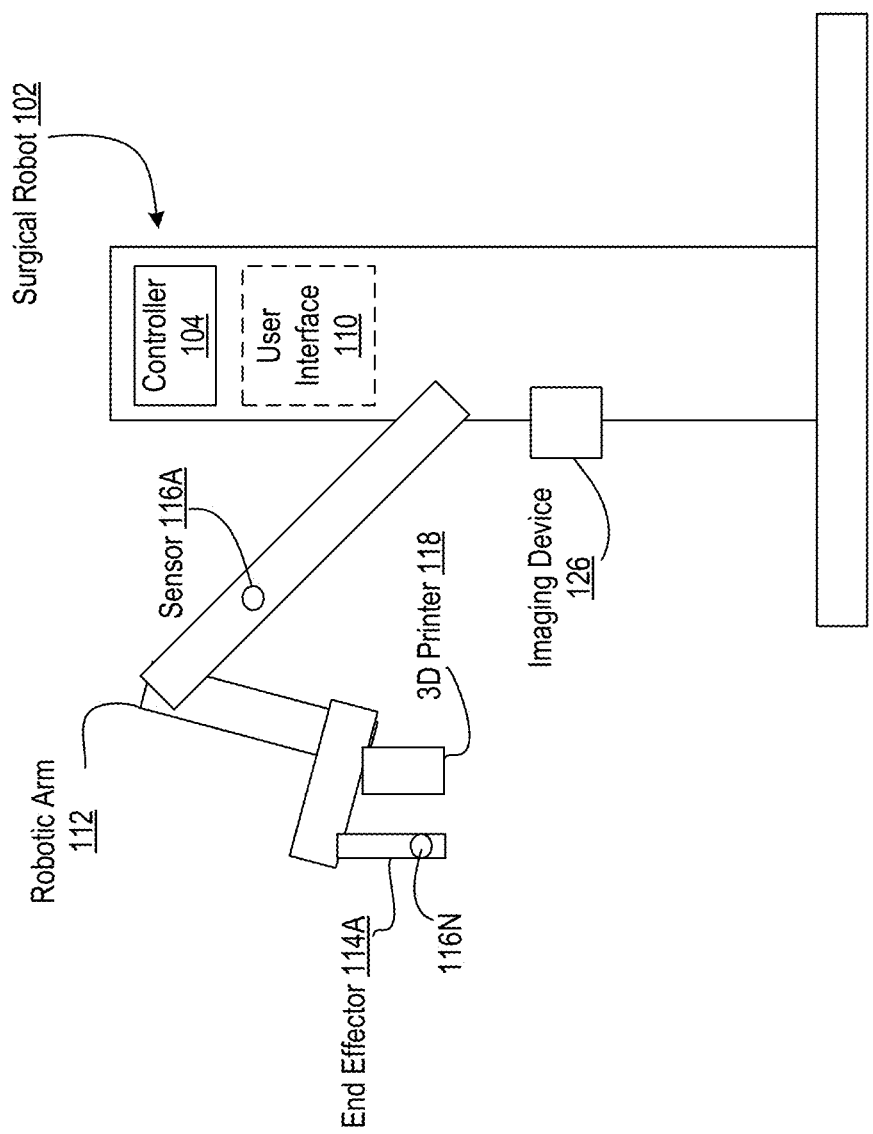
FIG. 1C is another example surgical robot for performing in situ 3D printing of an implant during a surgical procedure.
Figure 1D:
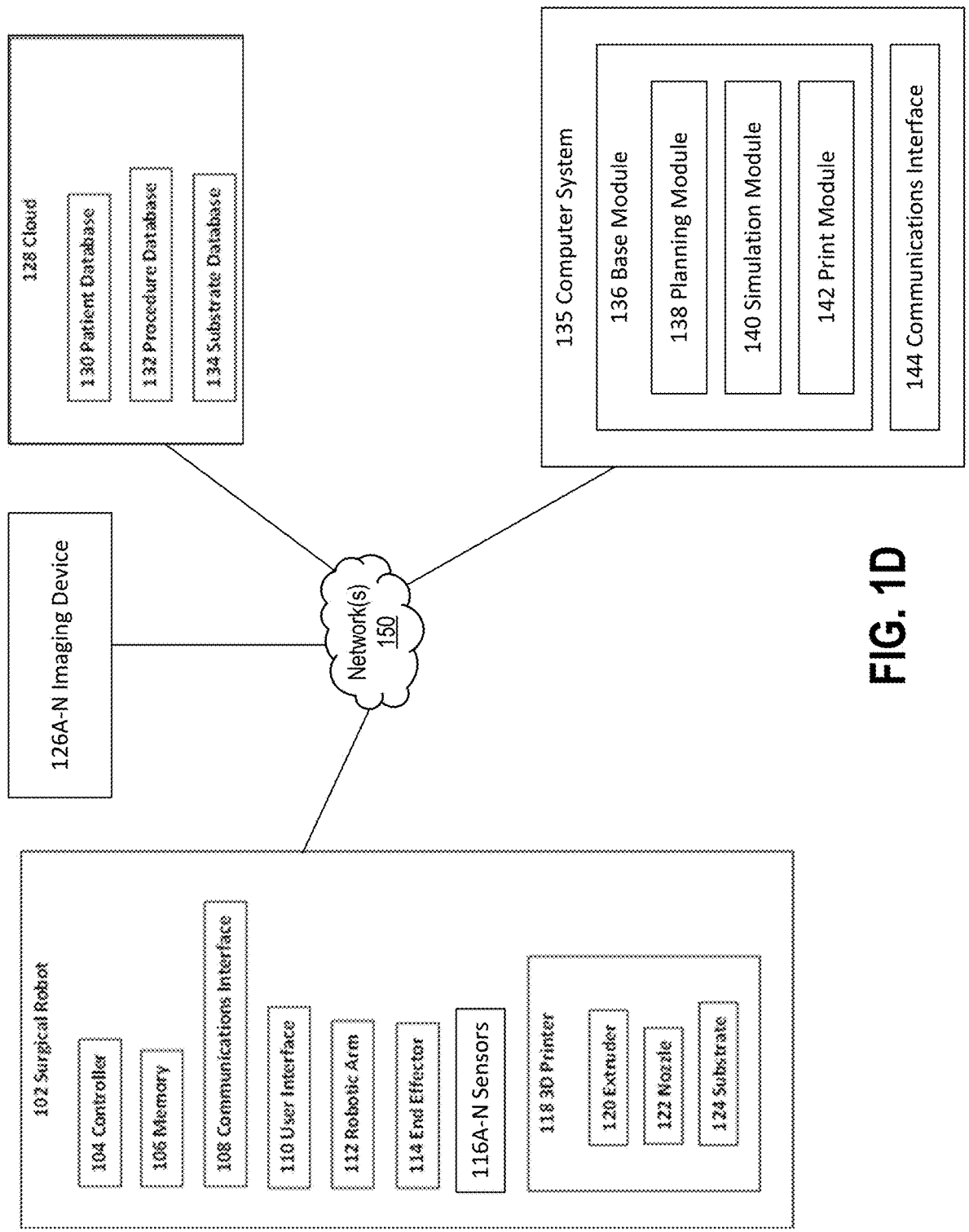
FIG. 1D illustrates example system components for performing in situ 3D printing of an implant during a surgical procedure.

FIG. 1C is another example surgical robot 102 for performing in situ 3D printing of an implant during a surgical procedure. In FIG. 1C, the surgical robot 102 includes one robotic arm 112. The surgical robot 102 also includes the imaging device 126, which can be attached to/integrated into any portion of the surgical robot 102 and/or any component of the surgical robot 102. One or more additional imaging devices can also be attached to the surgical robot 102. Here, the surgical robot 102 includes sensors 116A-N, at least one end effector 114A, and the 3D printer 118. Any of the components 116A-N, 114A, and 118 can be positioned in/attached to various other portions of the surgical robot 102.

In some implementations, the 3D printer 118 can include the imaging device 126. The 3D printer 118 can also include at least one of the sensors 116A-N. In some implementations, the end effector 114A can include the 3D printer 118. In some implementations, the imaging device 126 can be part of/attached to the robotic arm 112 and/or the end effector 114A. One or more other configurations of the surgical robot of FIG. 1C are also possible.

FIG. 1D illustrates example system components for performing in situ 3D printing of an implant during a surgical procedure. The surgical robot 102, imaging devices 126A-N, cloud 128, and computer system 135 can communicate (e.g., wired and/or wireless) via network(s) 150. The surgical robot 102 can be a robotic system designed to assist a surgeon or other medical professional in performing a surgical procedure (e.g., operation) on a patient. The surgical robot 102 may include a controller 104, memory 106, communication interface 108, user interface 110, at least one robotic arm 112, at least one end effector 114 (e.g., attached to or part of at least one robotic arm 112), sensors 116A-N, and a 3D printer 118.

Any one or more of the components 104, 106, 108, 110, 112, 114, 116A-N, and/or 118 may be part of/integrated into the surgical robot 102 or communicably connected to/coupled with the surgical robot 102. For example, the user interface 110 can be a separate component from the surgical robot 102. The user interface 110 can be part of a user device that is used by the surgeon. The surgeon can be remote from a site of the surgical procedure. Therefore, the user interface 110 can be remote and separate from the surgical robot 102 but in communication (e.g., wireless) with the surgical robot 102 via the network(s) 150. As another example, one or more of the sensors 116A-N can be part of the surgical robot 102 and separate from the surgical robot 102. Some of the sensors 116A-N can be connected to/integrated into other devices used during the surgical procedure. In some implementations, one or more of the sensors 116A-N can also be inserted into or otherwise worn by/attached to a patient.

The controller 104 can be a computing device to control the at least one robotic arm 112 and the end effector 114 of the surgical robot 102. The controller 104 can also include a processor. The controller 104 can communicate with the memory 106 for performing computations and for storing data. The controller 104 can be any type of central processing unit (CPU) or graphical processing unit (GPU), including but not limited to generally available CPUs or GPUs and/or custom/purpose-build CPUs or GPUs. In some implementations, more than one controller 104 may operate in tandem and may be of different types, such as one CPU and one GPU. A GPU may not be restricted to only processing graphics or image data. The GPU can also be used for other computations.

The memory 106 can include electronic circuitry that temporarily stores data for usage by the controller 104. The memory 106 may additionally include persistent data storage for storing data used by the controller 104. The memory 106 may be integrated into the controller 104 or may be a discrete component. The memory 106 may be integrated into a circuit, such as a soldered-on component of a single board computer (SBC) or may be a removable component, such as a discrete dynamic random-access memory (DRAM) stick, secure digital (SD) card, flash drive, solid state drive (SSD), magnetic hard disk drive (SSD), etc. Various types of memory 106 may be used by the surgical robot 102.

The communications interface 108 can be configured to provide communication between the system components described herein. The communications interface 108 also can allow the surgical robot 102 to communicate with external devices. The communications interface 108 may include a wireless antenna and transceiver and/or a port for receiving a cable to facilitate a wired connection. Examples of a wired connection can include ethernet, universal serial bus (USB), and/or a proprietary connection. A wireless communications interface 108 may include, for example, any of WIFI, BLUETOOTH, near field communications (NFC), and/or a cellular communications interface such as 3G, 4G, LTE, 5G, etc.

Moreover, the communications interface 108 can provide for transmitting and receiving data to and from the cloud 128 for purposes of training artificial intelligence techniques/algorithms used for operating the surgical robot 102. The communications interface 108 can also be used to receive remote commands from a remote user (such as when the user interface 110 is part of a user device of the surgeon and the surgeon is remote from the physical site of the surgical procedure). The communications interface 108 can also be used to receive and transmit artificial intelligence techniques/algorithms already existing external to the surgical robot 102 for use during runtime operation of the surgical robot 102 during the surgical procedure.

The user interface 110 can present information about the surgical procedure to the surgeon. The user interface 110 can also accept control inputs from the surgeon. The control inputs can be translated into instructions that, when executed by the controller 104, cause the surgical robot 102 to perform user-defined actions. The user interface 110 can include any type of input device, including but not limited to a keyboard, mouse, trackball, joystick, wireless or wired gamepad, sliders, scroll wheels, touch screen, microphone, etc. The user interface 110 can accept direct inputs, such as from a joystick controlling the movement of the robotic arm 112, and/or indirect inputs, such as commands entered on a keyboard or touchscreen, such as adjusting sensitivity of a joystick control or the speed of the robotic arm 112 movement in response to the joystick. The user interface 110 may also include a display screen for presenting information to the surgeon, such as patient status, imaging data, and navigation data. In some implementations, the user interface 110 can also include speakers for providing auditory feedback. The user interface 110 may also utilize haptics to provide feedback to the surgeon. In some implementations, the user interface 110 can be any type of computing device, including but not limited to a mobile device such as a smartphone, laptop, tablet, mobile phone, wearable device, and/or computer.

The at least one robotic arm 112 can be a mechanically actuated arm or lever with at least two degrees of freedom. The robotic arm 112 can include at least one end effector 114 and/or one or more imaging devices 126A-N. The robotic arm 112 may additionally be capable of changing the end effector 114 to facilitate multiple functions and operation of a variety of tools. For example, the surgeon or another relevant user can swap out the end effector 114 on the robotic arm 112 for another tool, such as a scalpel or laser.

The robotic arm 112 can be controlled in a variety of modes. For example, the robotic arm 112 (or at least one of the robotic arms 112) can be manually controlled (e.g., by the surgeon at the user interface 110). The robotic arm 112 can also be autonomously controlled (e.g., by the computer system 135 and/or the controller 104). The robotic arm 112 can also be or semi-autonomously controlled (e.g., by the computer system 135, the controller 104, and/or the surgeon at the user interface 110). As described herein, the surgical robot 102 may have one robotic arm 112 or multiple robotic arms 112, each of which may be operated independently by one or more users, autonomous systems (e.g., the computer system 135) and/or a combination of users and computing systems.

The end effector 114 can be attached at an end of the robotic arm 112 and configured to perform one or more operations during the surgical procedure. The end effector 114 can be a tool or device for interacting with a physical object. For example, the end effector 114 can be a surgical tool intended for acting upon or within the patient. The end effector 1104 can also be a gripping device for securing another surgical tool to the robotic arm 112 (or another portion of the surgical robot 102). In some implementations, the end effector 114 may be permanently affixed to the end of the robotic arm 112. In some implementations, the end effector 114 may be detachable, thereby allowing for a system of interchangeable end effectors 114 to be applied to the robotic arm 112. This can also be beneficial to select and swap a single robotic arm 112 with multiple robotic arms 112 or other types of robotic arms. In some implementations, the end effector 114 can be the 3D printer 118 described further below.

The sensors 116A-N can provide feedback to the surgeon and/or the artificial intelligence techniques used by the surgical robot 102. The feedback can include data indicating operation of components of the surgical robot 102. The feedback can include health data about the patient during the surgical procedure. The feedback can also include location information about components of the surgical robot 102, such as positioning of at least one robotic arm 112 relative to an incision point in the patient and/or a desired location for an implant in the patient. The feedback provided by the sensors can then be used to refine any of the techniques described herein. For example, the feedback can be fed into the artificial intelligence techniques described herein and used to refine a shape or size of the implant to be 3D printed inside, affixed to, adjacent, or otherwise around a particular structure inside the patient's body. The feedback can provide valuable data for real-time or near real-time adjustment of the 3D printing techniques described herein to ensure accuracy in performing the surgical procedure and improved safety of the patient.

As described above, the sensors 116A-N can be measurement tools for monitoring characteristics and/or metrics associated with the surgical robot 102, end effector 114, 3D printer 118, and/or patient. One or more of the sensors 116A-N can be discrete or part of an array or assembly, such as integrated into a print head of the 3D printer 118. One or more of the sensors 116A-N can include, but are not limited to, an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc.

The sensors 116A-N can be integrated into operation of the surgical robot 102 and/or can monitor status and health of the patient before, during, and/or after the surgical procedure. Data acquired by the sensors 116A-N can be used to train one or more machine learning algorithms used by the surgical robot 102 and/or artificial intelligence to control the surgical robot 102.

The 3D printer 118 can include least an extruder 120, nozzle 122, and a supply of substrate 124. During operation, the substrate 124 can be drawn from a supply by the at least one extruder 120. The supply can be one or more reservoirs, a spool of filament, a hopper of raw pellets, etc. part of the 3D printer 118, part of the surgical robot 102, or separate from the 3D printer 118 or surgical robot 102. The extruder 120 can then force the substrate 124 through the nozzle 122, which deposits a controlled amount of the substrate 124 onto a print site. Here, the print site can be a desired location at least partially or wholly inside or within the patient's body. The 3D printer 118 can deposit material onto the print site at any desired position and/or orientation.

The 3D printer 118 may be a stand-alone machine or can be integrated into the end effector 114 of the surgical robot 102. In some implementations, the 3D printer 118 can be attached to the surgical robot 102 and can be separate/independent from the end effector 114. The 3D printer 118 may store the substrate 124 externally and may feed the substrate to a print head that includes at least the nozzle 122, via a conduit that can be run along or through at least part of the robotic arm 112. The extruder 120 can be a component of the 3D printer 118 as described above that can receive the substrate 124 from a reservoir, spool, hopper, etc. and advance the substrate 124 through the nozzle 122. The extruder 120 can control a rate of flow of the substrate 124 through the nozzle 122.

In some implementations, the extruder 120 may also function as a mixer to combine or agitate one or more substrates 124. For example, a substrate 124 having a two-part resin epoxy may be combined and mixed by the extruder 120 prior to being advanced to the nozzle 122 for 3D printing inside or within (at least partially or wholly) the patient's body during the surgical procedure. A mixer, if needed, may also be a separate component that can combine or agitate the one or more substrates 124 prior to being received by the extruder 120. Multiple extruders 120 may also be utilized, with one being positioned between a supply of the substrate 124 and a mixer and a second being positioned between the mixer and the nozzle 122. Further implementations of the 3D printer 118 can include a plurality of extruders 120, each paired with a nozzle 122.

Multiple substrates 124 can also be combined to achieve a desired material property and/or to activate a desired chemical reaction for 3D printing inside, adjacent, affixed to, or otherwise around one or more anatomical structures of the patient's body. Multiple substrates 124 can alternatively be used in succession to achieve a composite component being made of different materials, each with its own physical properties.

In some implementations, the extruder 120 can be a pump. The nozzle 122 can be an orifice through which the substrate 124 can flow and be deposited on a print or printer surface (e.g., a desired location inside the patient's body). The print surface can be a prepared surface of a patient's tissues, a synthetic surface, such as one or more implant components, and/or a previous layer of extruded substrate 124 including any material that may be applied to form an adhesion layer to promote adhesion of the substrate 124 to a base material. The base material may be the patient's tissues including but not limited to bone, skin, muscle, fascia, tendons, ligaments, blood vessels, etc.

The nozzle 122 can be cast or machined from metal or plastic as a single piece. The nozzle 122 can also include multiple components. In some implementations, the nozzle 122 may be capable of dynamically increasing and/or decreasing an orifice size. The nozzle 122 can additionally be capable of articulating to achieve a range of orientations independent of movement by the robotic arm 112. The nozzle 122 may also include multiple orifices. In some implementations, multiple nozzles 112 may be supplied by one extruder 120.

As described above, the substrate 124 can be a material dispensed by the 3D printer 118. The substrate 124 may be dispensed as a liquid that can be heated, mixed, or otherwise prepared to be applied via the extruder 120 and the nozzle 122. The substrate 124 may alternatively be dispensed as a solid, powder, and/or gas. The substrate 124 may be capable of bonding to the patient's tissues, synthetic surfaces, the same substrate 124, and/or other substrates 124. The substrate 124 can be chosen for any number of physical properties including but not limited to types of surfaces or materials to which the substrate 124 will or will not readily adhere to. Special adhesive materials can be applied and/or dispensed to promote adhesion between a print surface, such as the patient's tissues, and the substrate 124. Such materials can include adhesives, such as glues, and can be applied via the 3D printer 118 or other suitable means.

In some implementations, the substrate 124 can include one or more adhesive materials. For example, the substrate 124 for printing within the patient's body can have properties of being non-toxic. Moreover, the substrate 124 can include properties that do not cause a rejection response by the patient's body. Such properties may be specific to the patient, such as in the case of the patient having an allergy or sensitivity to a particular type of material. Examples of biocompatible substrates 124 include, but are not limited to, alumina, bioglass, cobalt-chromium alloy, hydroxyapatite, medical-grade silicone, polyvinylchloride (PVC), polyethylene (PE), polypropylene (PP), polytetrafluoroethylene (PTFE), polymethylmethacrylate (PMMA), stainless steel, trimethyl carbonate, TMC NAD-lactide, titanium and titanium alloys, zirconia, etc.

In some implementations, the substrate 124 can include a thermoplastic, preferably with a low melting point (e.g., a melting point below a predetermined threshold value). When thermoplastics are used, a hot end of the thermoplastics may be positioned between the extruder 120 and the nozzle 122. In some implementations, metals can also be used as a powder or mixed with a binder, such as in a filament or resin. A laser sintering process can also be used to bond the material(s) for the substrate 124. In some implementations, a resin may be used that can require mixing a first part and a second part of materials to initiate a chemical reaction that causes the combined material to harden. Either part of a two-part resin may be a liquid and/or a pliable solid, such as a resin clay material. Additional additives may be mixed with a traditional two-part resin to achieve the desired physical properties. Some resins may cure when subjected to a UV light. In such implementations, a UV light source may be affixed to and/or integrated into the 3D printer 118, the end effector 114, and/or the nozzle 122 to cure the substrate 124 deposited by the 3D printer 118. The UV light source can otherwise be positioned near the surgical robot 102 for curing purposes.

The imaging devices 126A-N can include any device capable of collecting data that can be used to create an image, video, and/or representation of a physical structure or phenomena. One or more of the imaging devices 126A-N can also collect sound and/or electromagnetic waves and assemble a visual representation of the detected waves for further processing by the computer system 135. The imaging devices 126A-N can collect waves from any part of an electromagnetic spectrum and/or sounds at any range of frequencies, often as a matrix of independently acquired measurements that each represent a pixel of a two and/or three-dimensional image. These measurements may be taken simultaneously and/or in series via a scanning process or a combination of methods. Some pixels of an image produced by the imaging devices 126A-N may be interpolated from direct measurements representing adjacent pixels in order to increase the resolution of a generated image.

The imaging devices 126A-N can include, for example, cameras attached to the at least one robotic arm 112, cameras mounted to a ceiling or other structure above a surgical theater or location of the surgical procedure, cameras mounted on a tripod or other independent mounting device, cameras worn on the body of the surgeon or other relevant users during the surgical procedure, cameras incorporated into a wearable device, such as an augmented reality device like GOOGLE GLASS, MICROSOFT HOLOLENS, etc., cameras integrated into an endoscopic, microscopic, laparoscopic, or any camera or other imaging device (e.g. ultrasound) that may be present during the surgical procedure, etc.

In some implementations, the imaging devices 126A-N can include any algorithm and/or software module capable of determining qualitative and/or quantitative data from medical images. The algorithms can include, for example, a deep learning algorithm that has been trained on a dataset of medical images. The deep learning algorithm can be trained to identify, extract, label, and/or score particular features in the medical images, such as structures inside the patient's body, implants, and/or surgical devices (e.g., the end effector 114, the robotic arm 112, and/or the surgical robot 102). One or more of the imaging devices 126A-N can also further refer to devices used to acquire medical imagery by means including, but not limited to, magnetic resonance imaging (MRI), computed tomography (CT), X-Ray, positron emission tomography (PET), ultrasound, arthrography, angiography, myelography, etc.

The cloud 128 can be a distributed network of computers including servers and/or databases. The cloud 128 can be a private cloud, where access is restricted by isolating the network, such as preventing external access, or by using encryption to limit access to only authorized users. Alternatively, the cloud 128 can be a public cloud where access is widely available via the internet or other network communications. In some implementations, the cloud 128 can be a database, data store, or other device or cloud-based system for storing quantities of data. The cloud 128 can, for example, include a patient database 130, procedure database 132, and substrate database 134.

The patient database 130 (see FIG. 2) can store patient data including but not limited to electronic medical records, diagnosed conditions, patient specific baseline values, such as heart rate, blood pressure, etc., and medical imaging data. The patient database 130 can additionally include personal identifiable information, insurance and billing information, personal contact information, and emergency contact information. The patient database 130 can also contain legal documentation such as consent to perform one or more surgical procedures. The patient database 130 may further include familial relationships and genetic data to facilitate a comprehensive family history.

In some implementations, the patient database 130 can also store medical images that can be used by the computer system 135 to determine aspects of the patient's anatomy that affect the surgical procedure and/or a 3D printed implant. The medical images may additionally include annotations from a practitioner and/or algorithm (e.g., machine learning, artificial intelligence) that can indicate tissue types, structures, and/or other anatomical features that can be used by the computer system 135 to modify the surgical procedure and/or the 3D printed implant.

The procedure database 132 (see FIG. 3) can store data related to surgical or therapeutic procedures, including a type of procedure, actions taken during the procedure, what is treated by the procedure, possible contraindications or complications, and resources required for the procedure, such as personnel, hard goods, and consumables.

The substrate database 134 (see FIG. 4) can store data related to the 3D printer substrates 124, such as physical properties of the printed material, physical properties of the material prior to extrusion, actions required for extruding the substrate 124, such as mixing or heating, requirements for curing, such as environmental conditions and time, and materials with which it will or will not readily bond. The substrate database 134 can contain materials and corresponding physical properties that may not be intended to be used as the substrates 124, such as materials which may be toxic or illicit a rejection response by the body. Such materials may also include body tissues such as bone, muscle, fascia, skin, etc. Viewing these types of materials in the database 134 can be beneficial to ensure that only materials that are safe for the patient's body may be used in 3D printing an implant for that patient.

The computer system 135 can include one or more components or modules to perform the techniques described herein. In some implementations, the computer system 135 can be a cloud-based system. For example the computer system 135 can be part of the cloud 128. In some implementations, as shown in FIG. 1D, the computer system 135 can be separate from the cloud 128. The computer system 135 can be a remote computing system and/or network of computing systems configured to generate instructions to accurately and safely print a 3D implant inside, adjacent, affixed to, or otherwise around a patient's body during a surgical procedure. Accordingly, the computer system 135 can include a base module 136 having a planning module 138, a simulation module 140, and a print module 142. The computer system 135 can also include a communications interface 144 to provide communication between and amongst the system components described herein.

The base module 136 (see FIG. 5) can acquire images of the patient's anatomy from the imaging devices 126A-N or from the patient database 130 in the cloud 128. These images can be transmitted to the planning module 138 (see FIG. 6) for use in designing a structure (e.g., implant) to be 3D printed directly within the patient during the surgical procedure. The images can also be used by the planning module 138 to generate 3D printing instructions for execution by the 3D printer 118 during the surgical procedure.

The base module 136 can then receive the 3D printing instructions from the planning module 128 and send the instructions to the simulation module 140. The simulation module 140 (see FIG. 7) can receive the 3D printing instructions, image data acquired by the imaging devices 126A-N, and further can query the procedure database 132 for data relating to the procedure to be simulated. Any issues identified during simulation can be compiled into an error report. A successful simulation result or the error report can then be received by the base module 136. If an error report is received, the base module 136 can trigger the planning module 138 to modify the instructions.

Otherwise, the base module 136 can send the instructions to the print module 142 (see FIG. 8), which can prepare the print surfaces, apply an adhesion layer if necessary, and apply the substrate 124 to the print surface in runtime, during the surgical procedure. The print site can be periodically and/or continuously imaged by the imaging devices 126A-N to monitor progress of the 3D printing inside or within (at least partially) the patient's body, until the printing is complete. When the print is complete, a completion status can be received by the base module 136 and the procedure can end.

As mentioned above, the planning module 138 can receive imaging data of the patient acquired by at least one of the imaging devices 126A-N from the base module 126. The imaging data can be used to identify appropriate print surfaces onto which the 3D printed structure can be constructed inside or within (at least partially) the patient's body. The imaging data can also be used to identify properties of the print surfaces and surrounding structures, such as any sensitive structures that may need to be avoided by the surgical robot 102 components during the surgical procedure, including but not limited to structures that represent hard tissues and those that represent soft tissues.

The planning module 138 can also query the procedure database 132 and retrieve information for at least one procedure to be completed. The procedure information may include an initial design of the structure or implant to be printed, navigation data to guide the end effector 114 of the surgical robot 102 to the print site/surface, etc. The retrieved data can be used to create a print design, which may be a clean-sheet design, a customization of an existing design, and/or a refinement of a rough drawing created by a surgeon or other medical professional. The planning module 138 further can query the substrate database 134 and select at least one substrate 124 to be used to print the designed structure. The planning module 138 then can generate 3D printing instructions and send those instructions back to the base module 136.

The simulation module 140 can then receive the 3D printing instructions prepared or modified by the planning module 138. The simulation module 140 can also receive imaging data acquired of the patient and data queried from the procedure database 132. Using this information, the simulation module 140 can simulate the procedure to be performed. The simulation can include navigating at least one end effector 114 affixed to the robotic arm 112 of the surgical robot 102 to the print site inside, adjacent, affixed to, or otherwise around one or more anatomical structures of the patient's body. The end effector 114 can include at least one 3D printer 118 for extruding the substrate 124 onto the print site.

If the simulation is successful, a successful result can be sent by the simulation module 140 to the base module 136. If the simulation encountered any issues, faults, warning, etc., such events can be compiled into an error log or otherwise flagged/tracked and then sent to the base module 136. The error log can then be used by the planning module 138 to improve or otherwise adjust the 3D printing instructions. The simulation module 140 can simulate the improved 3D printing instructions to test whether the originally flagged issues have been resolved. If the issues have been resolved, then the improved 3D printing instructions can be executed during runtime in the surgical procedure. If the issues have not been resolved, the computer system 135 can keep running through updating and simulating the 3D printing instructions until the issues are resolved.

The print module 142 can receive final 3D printing instructions to be executed, from the base module 136. The print module 142 can be configured to prepare print surfaces, which may include any actions of a surgical procedure preceding the print operation, such as making incisions, accessing an interior of the patient, etc. Preparation of the print surfaces may additionally include removing soft tissues to expose hard tissues, such as bone, cleaning a surface and drying the surface of the patient's body, etc. The print module 142 can also be configured to apply an adhesion layer prior to application of the primary substrate 124 materials. The substrate 124 can be extruded onto the print site and the print site can be periodically and/or continuously imaged to monitor the progress of the printing inside, within, or otherwise around the patient's body. When the printing is complete, a completion status can be returned to the base module 136. Information such as the completion status can then be transmitted to and presented at the user interface 110, to be viewed by the surgeon or other relevant medical professionals.

In some implementations, the computer system 135 can be part of the surgical robot 102. In some implementations, components of the computer system 135 can be in communication (e.g., wired and/or wireless) with the components of the surgical robot 102. For example, the print module 142 can be configured to generate instructions to be executed by the end effector 114 on the robotic arm 112 of the surgical robot 102. The instructions can cause the end effector 114 to, for example, prepare the print surface of the patient by cleaning an incision site of the patient's body, making the incision, removing tissues, and/or apply the adhesion layer prior to application of the primary substrate 124 materials. The print module 142 can also be configured to generate instructions to be executed by the 3D printer 118 of the surgical robot 102. For example, the instructions can cause the 3D printer 118 to apply the adhesion layer and then inject the substrate 124 at predetermined orientations and/or speeds onto the adhesion layer to build the implant or other structure within the patient's body. If the surgeon provides user input at the user interface 110 to control operation/actions of the end effector 114 and/or the 3D printer 118, the user input can be transmitted to the print module 142 and made into instructions to be performed by the components of the surgical robot 102. Any instructions generated by the print module 142 can be transmitted to the controller 104 of the surgical robot 102 for execution during runtime.

FIG. 2 illustrates example patient data in the patient database 130 used for in situ 3D printing implants during a surgical procedure. The patient database 130 can include data about one or more patients, which may also include electronic medical records. The patient database 130 can include personally identifiable information, such as name, date of birth, address, insurance information, etc. of each patient. The patient database 130 may additionally include information about a patient's health or medical history, such as diagnosed conditions, allergies, medications, normal baseline vital sign ranges for the patient, etc. The patient database 130 may be populated by medical professionals, such as a patients' physicians, specialists, such as surgeons, therapists, and/or any other medical professionals, including but not limited to nurses, emergency medical technicians, paramedics, etc.

The patient database 130 additionally can store images acquired by the base module 136 using at least one of the imaging devices 126A-N. The patient database 130 can also store data related to the patient from the planning module 138, simulation module 140, and/or print module 142. Moreover, the patient database 130 can be used by the planning module 138, simulation module 140, and/or print module 142 in performing any of their respective functions. For example, data about a patient stored in the database 138 can be used to generate 3D printing instructions by the planning module 138, where those instructions are specific to a size and/or shape of the patient (e.g., a smaller and thinner patient may require a smaller and shallower incision on a part of their body than a larger and heavier-set patient).

The patient database 130 can include, for example for each patient, medical images produced by the imaging devices 126A-N, which can include but are not limited to X-rays, CT (computed tomography) scans, positron emission tomography (PET) scans, Mill (magnetic resonance imaging), ultrasounds, nuclear medicine imaging, positron-emission tomography (PET), etc. Medical images can also include still images and/or videos from cameras that are external and/or internal to the patient, such as an endoscope, laparoscope, etc. Medical image data can also include metadata from the images, such as a specific model of equipment used to generate the image, date and time that the image was taken, geographic location of the image, anatomical location of the image, practitioner(s) who performed the imaging, etc. Additionally, the medical image data can include annotations from a practitioner and/or algorithm or other computer-implemented technique. The annotations can indicate tissue types, structures, and/or other anatomical features that can be used by the planning module 138, simulation module 140, and/or print module 142 to generate and modify the procedure and/or 3D printed implant.

In some implementations, the patient database 130 can also contain, for each patient, 3D anatomical representations of the patient generated by/from medical images, such as, for example, using cross-sectional imaging data provided by an Mill device to convert pixels from individual cross-sections into voxels that define a 3D volume. A computer system, such as the computer system 135, can extrapolate the volume between at least two pixels of at least two medical images to generate the 3D volume. The volume can be determined by a distance between cross-sections that the Mill device generated. The 3D anatomical representation may further be generated by the computer system by combining cross-sectional images from two or more axial planes of an imaging modality, such as MRI.

As an illustrative example, the patient database 130 can include an Mill scan of a male patient (M 0026), age 46. The MRI scan can show portions of the patient's hip joint that need to be replaced with prosthetic implants. The patient data may also include a prescription for removal and replacement of portions of the patient's pelvis and femur that form the patient's hip joint. The prescription might have been given primarily to relieve hip pain and stiffness caused by hip arthritis. The patient database 130 may further include a 3D model of the patient's hip joint and the prosthetic that needs to be implanted. This information can be retrieved by the components of the computer system 135 and used to accurately generate and modify 3D printing instructions of the prosthetic(s) to be implanted into the patient's hip joint before a surgical procedure to implant the prosthetic(s).

FIG. 3 illustrates example procedure data in the procedure database 132 used for in situ 3D printing implants during a surgical procedure. The procedure database 132 can include data about one or more procedures that can be performed by the components of the surgical robot 102 and/or the components of the computer system 135. The data in the database 132 can include, for example, steps for performing a particular type of surgical procedure and may also include alternative steps or responses to issues or complications that may arise during the procedure. The data can also include parameters and/or conditions by which the procedure may be halted or aborted during runtime. The data can also include actions taken, measurements taken such as vital signs, and personnel involved, including patient, surgeon, and any other personnel and equipment used for the particular type of surgical procedure. Such data can be useful for the planning module 138 to accurately generate 3D printing instructions that take into consideration various aspects of the procedure to be performed.

The procedure database 132 can be populated by surgeons, nurses, or any other medical professionals or technicians. The database 132 can also include relevant portions of patients' electronic medical records pertaining to a particular type of procedure to be performed for a particular patient. In some implementations, the procedure database 132 can additionally include patient data, such as the data in the patient database 130 (see FIG. 2) that may be relevant to one or more procedures.

The procedures represented by entries in the database 132 can include implant procedures and/or therapies that may involve injection or deposition of substances such that a 3D printed structure can be used to achieve the purpose of the procedures. The procedures can additionally include other in situ 3D printed procedures that may be performed using the techniques and systems described herein. The procedure database 132 can also include procedures that are not relevant to 3D printed procedures, in some implementations.

As described herein, the procedure database 132 can be used by the planning module 138 and/or the simulation module 140. As an illustrative example, the procedure database 132 can contain data about a hip joint replacement surgery. The procedure database 132 can indicate a procedure for a minimally invasive robotic surgery in which portions of a patient's pelvis and femur that form the patient's hip joint can be removed and replaced with a prosthetic implant. In such examples, the procedure data in the database 132 can include instructions to be generated by the planning module 138 and simulated by the simulation module 140 for minimally-invasive robotic 3D printing of the implant in situ. In another example, the procedure database 132 can store print data generated by the planning module 138.

FIG. 4 illustrates example substrate data in the substrate database 134 used for in situ 3D printing implants during a surgical procedure. The substrate database 134 can include information about the substrates 124 that can be selected by components of the computer system 135 and used by the 3D printer 118 to 3D print a structure within a patient during a surgical procedure. The substrate database 134 can include properties information for each of the substrates 124, their methods of application and curing, and/or safety data and/or manufacturer information. Some substrates can include two parts, such as a resin and hardener, which can cure after a working period that begins when the two components/parts are mixed. Other substrates may cure when exposed to a particular wavelength of light, such as ultraviolet. Further, some substrates may require heat to allow the material to be extruded, such as thermoplastics, while some substrates may be heated, melted, fused, bonded, etc. by a high intensity laser. Such information can be provided in the substrate database 134. The substrate database 134 may be populated by manufacturers of the substrates, such as via the cloud 128 depicted in FIG. 1D and/or a third-party database. The substrate database 134 can be used by the planning module 138 to generate accurate and precise 3D printing instructions involving use of particular substrates for particular procedures to be performed on particular patients.

Figure 5:
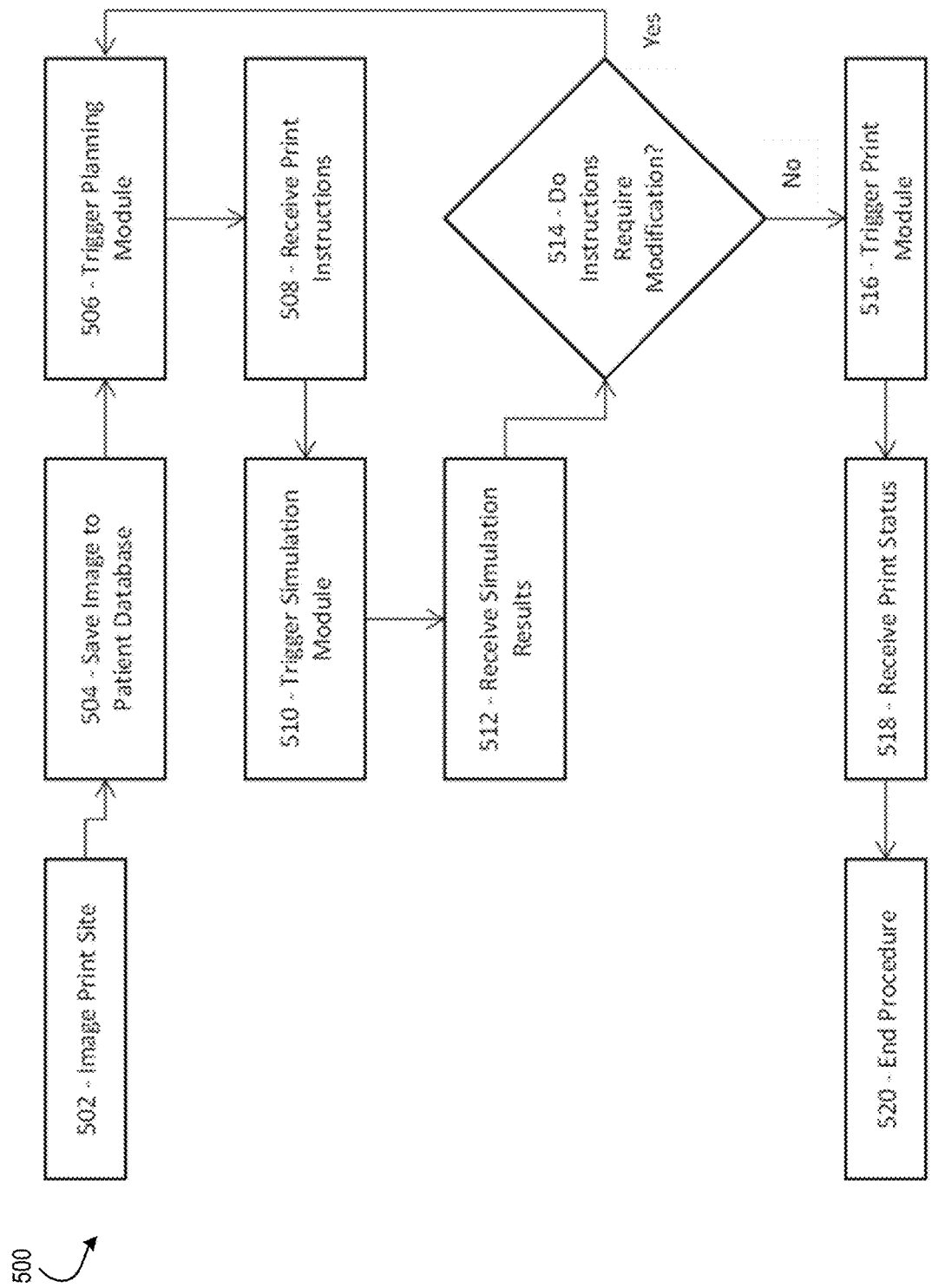
FIG. 5 is a flowchart of a process for preparing and performing in situ 3D printing of an implant during a surgical procedure.

FIG. 5 is a flowchart of a process 500 for preparing and performing in situ 3D printing of an implant during a surgical procedure. The process 500 describes functioning of the base module 136 of the computer system 135 shown in FIG. 1D. One or more blocks in the process 500 can be performed by one or more modules, engines, and/or computing systems. Moreover, the functions performed in the processes and methods described throughout this disclosure may be implemented in differing orders. Furthermore, the outlined blocks and operations are provided as examples, and some of the blocks and operations may be optional, combined into fewer blocks and operations, or expanded into additional blocks and operations without detracting from the essence of the disclosed technology.

The process 500 can begin with imaging of a print site, at block 502. One or more of the imaging devices 126A-N can image the patient, including the print site. The base module 136 can generate imaging instructions for execution by the one or more imaging devices 126A-N. The base module 316 can also request images captured by the one or more imaging devices 126A-N in block 502. As described herein, the imaging may be performed using at least one of any imaging method including both visual light and radiologic modalities. As an illustrative example, at least one imaging modality can be a radiologic modality such as CT, Mill, PET, etc. In some implementations, a single imaging modality may be used, such as Mill. In other implementations, multiple imaging modalities may be used, such as MRI, CT, and ultrasound. In some implementations, a single image frame may be used. In other implementations, multiple image frames may be used. Multiple images may be used to create a higher resolution 2D image of the print site in the patient's body. Similar techniques can also be applied in slices of varying depths, and/or from varying orientations to create a 3D representation of the print site.

In block 504, the base module 136 can save the captured image(s) to the patient database 130 (see FIG. 2). The image data may include raw data, such as individual image frames, and/or may include composite images or models made of multiple image frames. Sometimes, for example, a series of images acquired by an MRI of a patient's print site (e.g., their hip where a joint is to be replaced with an implant) can be received in block 502 and stored in block 504 by the base module 136.

The base module 136 can then send a notification to the planning module 138 in block 506, thereby triggering the planning module 138 to perform its operations. The base module 136 can send the image data to the planning module 138. Alternatively or additionally, the base module 136 can send a reference to a location in the patient database 130 where the image data is stored. Using the reference, the planning module 138 can then retrieve the image data from the patient database 130 for use in processing and further analysis.

The planning module 138 can use the image data to identify print surfaces and properties of the print surfaces within the patient's body. The planning module 138 further can query the procedure database 132 (see FIG. 3) and using data from the procedure database 132 to create a print design. The print design can be specific to characteristics of the particular patient undergoing the procedure, the characteristics being identified from the patient's image data and other patient data stored in the patient database 130. Furthermore, the planning module 138 can query the substrate database 134 (see FIG. 4) and select at least one substrate 124 with desired properties for use in the printed structure for the particular patient undergoing the surgical procedure.

Figure 6:
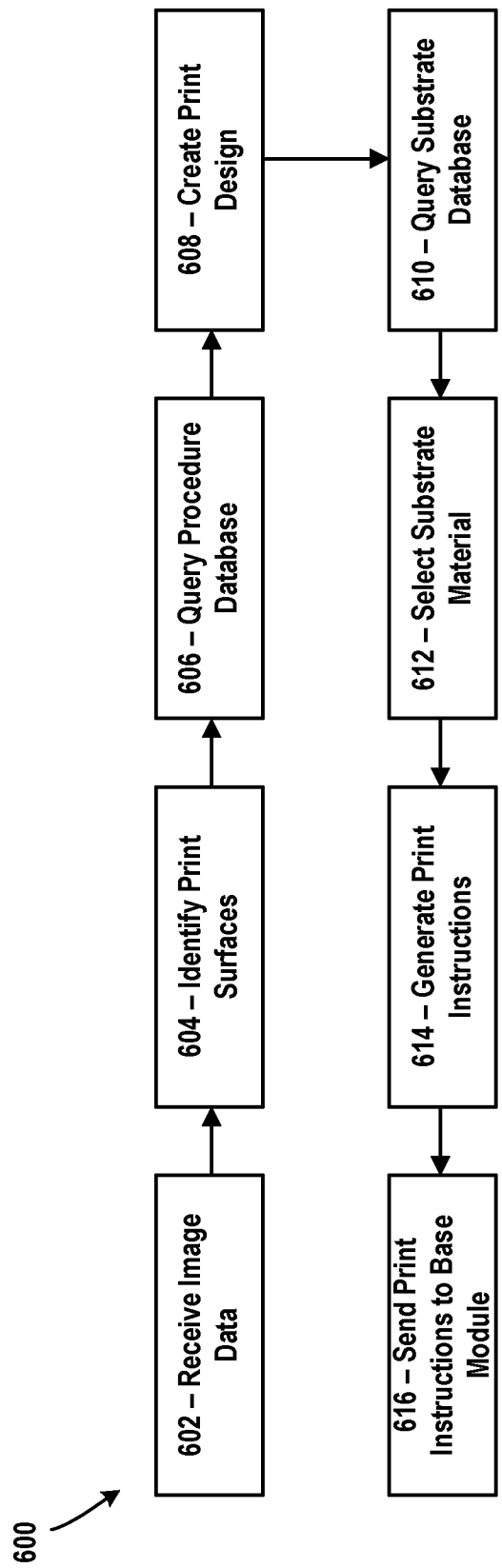
FIG. 6 is a flowchart of a process for preparing instructions for in situ 3D printing of the implant during the surgical procedure of FIG. 5.

The planning module 138 then can generate 3D printing instructions, as described further in FIG. 6, and return the instructions to the base module 136. The base module 136 can receive the instructions from the planning module 138 in block 508. The print instructions may include the design of the structure to be printed by the 3D printer 118 inside, within, or otherwise around the patient's body, which substrates 124 to use and where, which print surfaces are to be adhered to and which should remain unattached to the printed structure, etc. The print instructions may additionally include tool pathing for the 3D printer 118, end effector, 114, robotic arm 112, and/or any other tools utilized during the procedure. Similarly, the print instructions may include location and orientation information for adjusting the 3D printer 118, the nozzle 122, and settings for the extruder 120. The location and orientation information can be specific to the type of procedure, characteristics about the patient's body and health, characteristics about the print surface, and/or characteristics about the designed structure to be printed inside, adjacent, affixed to, or otherwise around anatomical structures of the patient's body.

Similarly, the print instructions may include instructions for use of the selected substrate 124, such as mixing a two-part resin, temperature to which to heat a thermoplastic, and/or the rates at which the substrate should be extruded. The print instructions may further include a method of curing the printed structure and tools and resources required, such as a source of ultraviolet light. Any of these instructions can be executed by an autonomous and/or semi-autonomous system, such as the computer system 135 and/or components of the surgical robot 102. In some implementations, one or more of these instructions can also be presented at the user interface 110 to one or more relevant medical professionals. The medical professional(s) can then manually perform one or more of the instructions and/or direct a computing system or other system described herein to perform the instructions.

Figure 7:
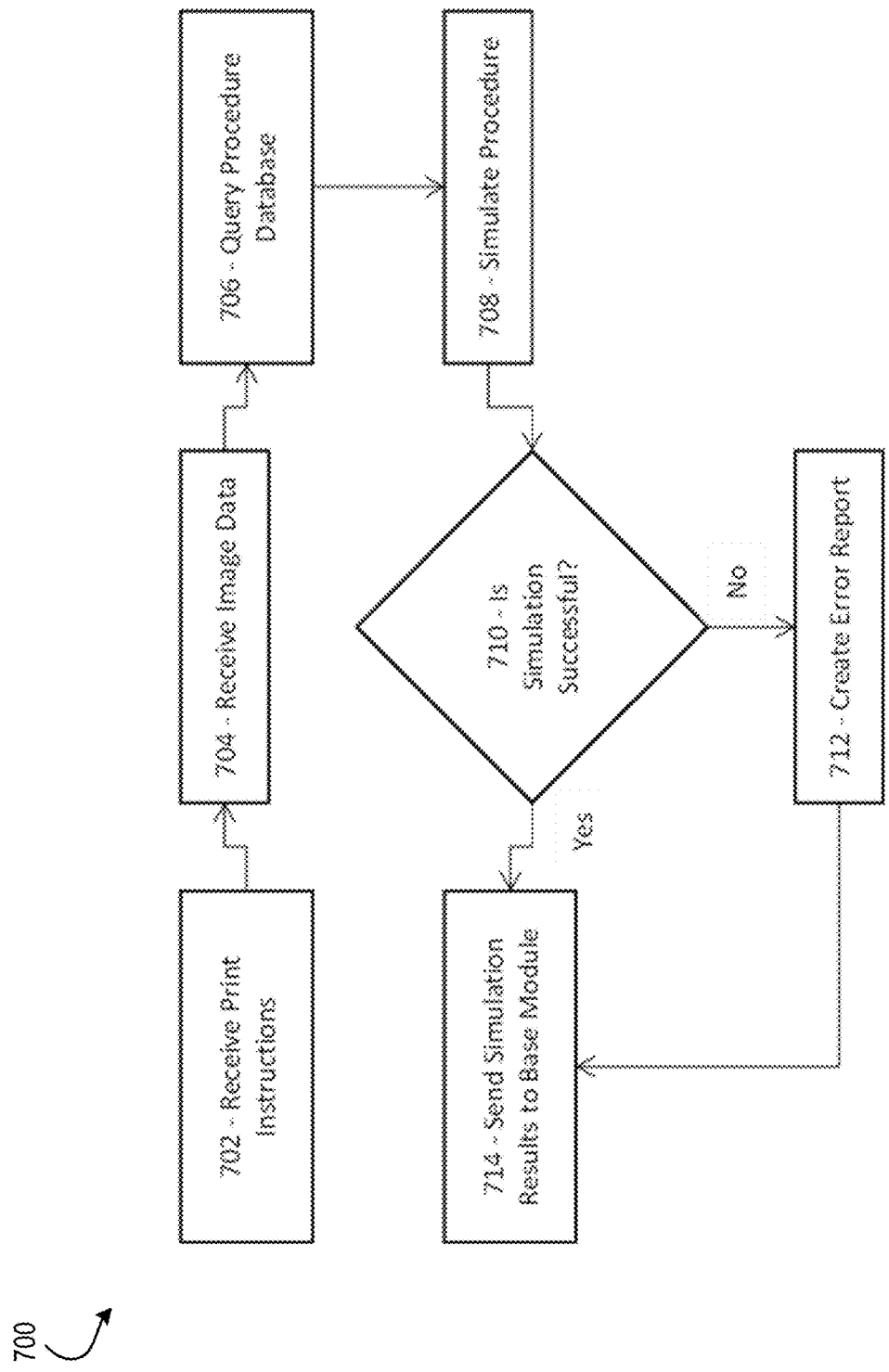
FIG. 7 is a flowchart of a process for simulating the in situ 3D printing of the implant during the surgical procedure of FIG. 5.

In block 510, the base module 136 triggers the simulation module 140 (see FIG. 7). The base module 136 can transmit the 3D printing instructions to the simulation module 140. In some implementations, the instructions can be stored in the procedure database 132 then accessed and retrieved by the simulation module 140. The simulation module 140 can also receive or retrieve image data and information about a type of procedure to be performed at the print site (e.g., from the procedure database 132). Examples of the procedure can include but are not limited to installation of an implant and/or reconstruction of a fractured or otherwise damaged bone.

The 3D printing instructions, image data, and procedure data are then used to perform a simulation of the procedure at the simulation module 140, including navigation of the robotic arm 112, end effector 114, 3D printer 118, and/or any other surgical tools that may be used during the procedure. The simulation module 140 can simulate passing such tools through the patient's body and printing the structure according to the 3D printing instructions inside, within, around, affixed to, or otherwise adjacent one or more portions of the patient's body. The simulation module 140 can simulate various scenarios in performing the procedure according to the 3D printing instructions and unique characteristics of the particular patient to predict/determine potential outcomes of the procedure. As a result, the simulation module 140 can determine and identify whether there are or may be any issues, such as with clearance of tools, during the procedure.

The simulation module 140 can accordingly generate a log of any issues found. The log of issues can be returned to the base module 136, and if no issues are found, a message indicating that simulation was successful can be returned to the base module 136. Accordingly, the base module 136 can receive simulation results from the simulation module 140 in block 512. The simulation results may include a message indicating a successful or unsuccessful simulation. In the event the simulation was unsuccessful, the base module 136 can receive a log of issues or an error log from the simulation module 140. As an illustrative example, the simulation results can include notification of an unsuccessful simulation and indicate at least one issue such as the nozzle 122 not having sufficient clearance to deposit the substrate 124 at approximately 35 minutes into the print. In some implementations, a log may be provided even if the simulation was successful, such as if the simulation identified some possible issues, but none of which may prevent the procedure from occurring, or which may be overcome at the discretion of the surgeon. In an implementations, the simulation results can include a success message, thereby indicating that the 3D printing instructions are effective and accurate to perform the procedure in the particular patient.

In block 514, the base module 136 can determine whether the 3D printing instructions require any modification. The instructions may need modification if the simulation results of block 512 were unsuccessful. In some implementations, the instructions may still require modification even if the simulation was successful if an accompanying log identified an issue that may be solved by optimizing the instructions, and/or if a supervising surgeon determines that an issue should be resolved.

If the simulation result was successful and there are no log entries, the instructions may not require modification and the base module 136 can proceed to block 516, described below. If the simulation was unsuccessful, the instructions may require modification and the base module 136 can return to block 506 and repeat the blocks 506-512 until the issues are resolved and/or no new issues arise during simulation. When returning to block 506, the base module 136 can provide the error log as part of the 3D printing instructions to the planning module 138 such that the planning module 138 can appropriately adjust the instructions to resolve the logged issue(s).

The modifications can include, for example, changing any of an end effector 114, nozzle 122, substrate 124, and/or position and/or orientation of any of the robotic arm 112, end effector 114, and/or nozzle 122. The modifications may also include alterations to the design of the structure, such as changing the substrates used, structural elements including infill, preparation of the print site including an adhesive layer, etc.

Referring now to block 516, the base module 136 can trigger the print module 142 (see FIG. 8) if the print instructions do not require modification. The print module 142 can receive final 3D printing instructions and execute those instructions by preparing the print surfaces, optionally applying an adhesion layer, and then applying successive layers of substrate 124 during runtime in the surgical procedure. For example, the print module 142 can generate and transmit instructions to perform these operations to the surgical robot 102. The controller 104 of the surgical robot 102 can then execute the operations in order to cause the 3D printer 118 to perform the 3D printing instructions during the procedure.

The print module 142 additionally can request the print site to be imaged by the one or more imaging devices 126A-N using visible light and/or radiologic imaging modalities. The images can then be used by the print module 142 to monitor progress of the 3D printer 118 until the printing is completed. Monitoring the print progress/status may include tracking the progress, such as tracking which layers have been printed, which layer is in the process of being printed, etc., in addition to tracking what region is being printed or has been printed (which may be represented as a quadrant, Cartesian coordinates, polar coordinates, etc.). The print progress may also include tracking quality, such as deviation of the print from the expected location. This tracking may be determined based on analysis of the print surface and/or may be tracked layer by layer, where an image of the printed layer can be compared against expected layer dimensions of the 3D model, from which a deviation is calculated. A deviation that is greater than a threshold value or tolerance level may indicate an error and be identified as such. Likewise, a deviation that is less than an error threshold value may require adjustments to the 3D printer to prevent compounding deviations that can cause an error condition. Similarly, error conditions may be identified based on identified deviations and/or any number of issues that may include, but is not limited to, print material supply runout, feed or nozzle clogging, mechanical failures, etc., which may be identifiable by a lack of material being deposited by the 3D printer, a lack of print material in the feed mechanism, reservoir, hopper, filament reel, etc. If multiple materials are used, for example, an error may be generated if the wrong material is used.

Sometimes, an error may be generated if the print head is in the wrong location, orientation, etc. An error may additionally or alternatively be generated if the patient's status changes, such as their vital signs exceed an operational range. An example of an operational range of vitals may be a heartrate between 50 and 120 beats per minute, an oxygen saturation above 95%, and/or a blood pressure with a systolic pressure between 95 and 130 mmHg. If the patient's vitals exceed the operational range, the 3D printer operation may be stopped until the patient is stabilized and the surgeon or other technician can resume the process.

Similarly, if error conditions are identified during the print process, the print process may be altered, such as by performing a calibration procedure to ensure the print head is properly aligned, or by stopping the print procedure and providing a notification to a surgeon or technician to inspect the system prior to resuming the procedure. In some instances, the print operation may be terminated when an error condition is identified, which may require removal of the 3D printer and/or restarting the print procedure. A check for quality may additionally or alternatively be performed after the 3D printing is completed. In some implementations, intervention by a surgeon or technician in response to an error condition may be replaced by an automated system intervention, which may include, but is not limited to, inspecting the print site, 3D printer, etc. and identifying and fixing the issue without intervention of the surgeon, operator, or other human operator.

At block 518, the base module 136 can receive a print status from the print module 142. The print status can include a message that the structure has been successfully 3D printed inside or within (partially or wholly) the patient's body during the procedure. In some implementations, the print status may be unsuccessful, and/or may require intervention by a surgeon or other relevant medical professional. The print status can be received at predetermined times during the procedure of printing the structure inside, near, connected to, or otherwise adjacent one or more portions of the patient's body. For example, the print status can be generated and received after each operation performed by the 3D printer 118. As another example, the print status can be received when the procedure starts and when the procedure ends. As another example, the print status can be received during the procedure only when a failure or issue arises during the procedure. The print status can be helpful to understand progress of the procedure and whether any failures arise that should be addressed during the procedure before the patient is harmed.

In the event of a failed print, for example, the print status can provide a notification indicating that the surgeon should remove some or all of the printed substrate inside or within (wholly or partially) the patient's body and then resume, restart, or end the procedure. In some implementations, the surgeon can review the notification and then accept the notification. Accepting the notification with user input at the user interface 110, for example, can cause components of the surgical robot 102, such as the end effector 114, to autonomously or semi-autonomously perform operations of removing the printed substrate inside, near, adjacent, and/or affixed to one or more portions of the patient's body. The surgeon can also provide user input to cause components of the surgical robot 102 to autonomously or semi-autonomously resume, restart, or end the procedure.

The base module 136 can end, at block 520, the procedure upon receiving a successful print status from the print module 142. Ending the procedure may include removing surgical tools from the patient and closing any incisions. Ending the procedure may additionally include any actions required during the procedure not previously mentioned to complete the surgical procedure and maintain the life and health of the patient. In an embodiment, removing all surgical tools from the patient can include removing the 3D printer 118, and closing all incisions made to provide access to the print site including to muscle, fascia, skin, etc. Additionally, ending the procedure in block 502 can include monitoring the patient for complications and managing any conditions that may present. Any of the operations of ending the procedure can be performed autonomously or semi-autonomously by the components described herein, such as the surgical robot 102. The base module 136 can generate instructions for the operations and transmit the instructions to the controller 104 of the surgical robot 102 for execution.

Moreover, monitoring the patient throughout the procedure and while ending the procedure can include pinging, by the base module 136, one or more sensors or other patient monitoring devices for vitals and other data about the patient. The base module 136 can monitor the received data from the sensors to determine if and when any of the monitored vitals of the patient drop below predetermined threshold values/ranges. If the vitals drop below the predetermined threshold values/ranges, the base module 136 can generate a notification to be presented at the user interface 110 to alert the surgeon of the patient's condition. The base module 136 can also generate instructions to be executed by one or more systems that improve the patient's condition.

FIG. 6 is a flowchart of a process 600 for preparing instructions for in situ 3D printing of the implant during the surgical procedure of FIG. 5. The process 600 can be performed by the planning module 138 described herein. One skilled in the art will appreciate that, for this and other processes and methods disclosed herein, the functions performed in the processes and methods may be implemented in differing order. Furthermore, the outlined blocks and operations are only provided as examples, and some of the blocks and operations may be optional, combined into fewer blocks and operations, and/or expanded into additional blocks and operations without detracting from the essence of the disclosed technology.

The process 600 begins with the planning module 138 receiving, at block 602, image data from the base module 136. Alternatively, the planning module 138 can receive a reference location or other identifying information for the image data in the patient database 130 from the base module 136. The planning module 138 can use the reference to facilitate retrieval of the image data from the patient database 130. As an example, the image data can include a series of MM images compiled into a 3D model of a patient John Smith's pelvis, specifically a right-side socket of the patient's ball joint where the femur meets the pelvis.

In block 604, the planning module 138 can identify print surfaces upon which substrate will be deposited by the 3D printer 118 to create a 3D printed structure inside or adjacent the patient's body. The print surfaces may be hard tissues such as bone and/or may be soft tissues such as skin, muscle, fascia, etc. In the above example of John Smith, the print surfaces are identified, by the planning module 138 as the right socket of the ball joint where the femur meets the pelvis, specifically where there are fractures and pieces missing from the joint, likely resulting from a trauma.

In some implementations, the print surface may be identified by a surgeon using a 3D computer-aided-design (CAD) system to map size, position, and orientation of the 3D print within the patient. The print surface may require preparation and may alternatively be imaged and mapped after the site is prepared. Machine learning may additionally or alternatively be used to map contours of the print surface and adapt the 3D print to conform to the contours of the print site. The adapted 3D print may additionally or alternatively be simulated to determine whether such adaptations may adversely impact the 3D print's performance.

The planning module 138 can also query, at block 606, the procedure database 132 for data about the procedure to be performed. In the above example of John Smith, the procedure to be performed can be a repair and reconstruction of the right socket of the ball joint where the femur meets the pelvis. Information about the procedure that is retrieved from the procedure database 132 can include instructions/steps for reinforcing the fractured bone and rebuilding missing pieces of the socket. The procedure data can also include incision locations, tool pathing, required resources including personnel and tools, etc. The procedure data may also include a type of implant or structure to be generated and implanted with 3D printing techniques.

The planning module 138 can then create, at block 608, a print design for the implant or structure to be printed directly inside the patient during the surgical procedure. The print design may be based on previous designs for similar implants and/or may be generated without an initial form. The print design can also be created based on unique characteristics to the particular patient, as identified in the patient database 130, such as bone density of the patient, weight of the patient, size of the patient, age of the patient, and other health metrics/data.

The print design may form a reconstructed natural structure, such as a bone, or may include an artificial structure, such as an implant, intended to reinforce and/or replace a natural structure such as a joint or part of a joint. The structure to be 3D printed may be intended to repair, reconstruct, reinforce, or support hard tissue structures, such as bone, and/or repair, reconstruct, replace, reinforce, and/or support soft tissue structures such as cartilage, ligaments, tendons, blood vessels, spinal disks, etc.

In some implementations, if a previous image of the patient's body (e.g., specifically, the print surface/site at least partially inside or otherwise within the patient's body where the implant or other structure is to be 3D printed) is available, prior to damage, the print design may be generated by the planning module 138 and based in part on the previous image data. Therefore, using current imagery and historical imagery can be beneficial for the planning module 138 to accurately identify structures to be reconstructed that match as closely as possible to structures that used to be in the patient's body, according to the historical imagery. In some implementations, if historical imagery is not available, simulations may be run by the planning module 138 (and/or the simulation module 140) to approximate dimensions of a structure to be 3D printed prior to injury.

In some implementations, the print design may create reinforcing structures such as bracing. The print design may additionally include a type and amount of infill to create an interior structure. Additionally or alternatively, the print design may include generation of material properties required for each part of the structure for use in selecting one or more substrates. In the example of John Smith, the planning module 138 can generate the print design for repair and reconstruction of the right pelvis socket of the ball joint where the pelvis meets the femur. The print design can include filling of fractures and reconstructing the joint based on simulated data using current imagery of John Smith's pelvis that is obtained by an Mill.

In block 610, the planning module 138 can query the substrate database 134 for substrates 124 matching material properties for the structure identified during generation of the print design. The substrates 124 may include those which match both physical properties of the structure when the substrate 124 is fully cured, and/or properties of the substrate 124 during the print process.

The planning module 138 can then select, at block 612, at least one substrate 124 to be used to print the print design. Material properties identified during creation of the print design may be used to select substrates suitable for manufacture of the structure at least partially inside or within the patient's body. Patient health conditions (e.g., allergies, sensitivity to certain materials, etc.) can also be used to select a suitable substrate for printing the structure at least partially inside or within the patient's body so that the patient's body does not reject the substrate or have an adverse effect.

In some implementations, one substrate may be selected, provided its properties are within a range of threshold properties required for the entire print design. In some implementations, multiple substrates may be selected to ensure a full range of material properties required by the print design are satisfied. The substrates may be selected for their material properties after being allowed to cure. The substrates can also be selected based on the printing process, such as viscosity of the material, to prevent undesired flow of the material during the print process, thereby ensuring patient health and safety during the surgical procedure. In the example of John Smith, the planning module 138 can select a UV curable resin, such as those used in dental procedures, and polymethylmethacrylate bone cement as an adhesive layer. Such selections can be made based on the print design generated in block 608 and health data/information about the patient.

In block 614, the planning module 138 can generate 3D printing instructions for use by the controller 104 to control in-situ printing of the print design by the 3D printer 118 affixed to the robotic arm 112. The instructions can include pathing (e.g., position, orientation, movement, speed of movement, angle of incision, angle of injection of substrate, etc.) for the robotic arm 112 and/or the nozzle 122 of the 3D printer 118. The instructions therefore can include position and orientation data for the nozzle 122 and/or extrusion rate for the extruder 120 to control an amount of substrate extruded. The instructions may include print speed and additional extrusion properties such as mixing, heating, or other preparation of the substrate as well as instructions for curing the substrate, such as by exposing the extruded substrate to ultraviolet light if the substrate is a UV curable resin.

In the example of John Smith, the 3D printing instructions generated by the planning module 138 can include providing the tool pathing, extrusion properties, and substrate curing parameters required to extrude and cure a UV curable resin to reconstruct the right ball joint socket of Joe Smith's pelvis. Sometimes, the instructions can include G-code or other similar programming languages used by 3D printers and CNC machines to provide instructions.

The planning module 138 can send, at block 616, the 3D printing instructions to the base module 136. The instructions can then be transmitted to the simulation module 140 for testing and validation before runtime use during the surgical procedure. If the instructions have already been tested and validated, the instructions can then be sent to the controller 104 of the surgical robot 102 for runtime execution during the patient's surgical procedure. As described above, the 3D printing instructions can include tool pathing for controlling movement of the robotic arm 112, and properties of the 3D printer 118, including but not limited to extrusion rate, position, and orientation of the nozzle 122, and parameters for curing the substrate, such as an exposure time (e.g., 15 second exposure times) to ultraviolet light after each layer of substrate is deposited on the print surface inside, within, or that is part of the patient's body.

FIG. 7 is a flowchart of a process 700 for simulating the in situ 3D printing of the implant during the surgical procedure of FIG. 5. The process 700 can be performed by the simulation module 140. One skilled in the art will appreciate that, for this and other processes and methods disclosed herein, the functions performed in the processes and methods may be implemented in differing order. Furthermore, the outlined blocks and operations are only provided as examples, and some of the blocks and operations may be optional, combined into fewer blocks and operations, and/or expanded into additional blocks and operations without detracting from the essence of the disclosed embodiments.

The process 700 begins with the simulation module 140 receiving, at block 702, 3D printing instructions from the base module 136. The instructions may include design of the structure to be printed by the 3D printer 118, which substrates to use and where, which print surfaces are to be adhered to and which should remain unattached to the printed structure, etc. The instructions may additionally include tool pathing for the 3D printer 118, end effector 114, robotic arm 112, and/or any other tools utilized during the surgical procedure. Similarly, the instructions may also include location and orientation of the 3D printer 118, nozzle 122, and/or settings for the extruder 120. The instructions may also include instructions for use of the selected at least one substrate, such as mixing a two-part resin, the temperature to which to heat a thermoplastic, and/or the rates at which the substrate should be extruded. The print instructions may further include a method of curing the printed structure and the tools and resources required, such as a source of ultraviolet light. In the example of John Smith, the print instructions can include a design for an implant fused to the pelvis of John Smith and reconstructing the socket of the hip joint. The print instructions can include an adhesive layer having polymethylmethacrylate bone cement and the substrate can be identified as a UV curable resin similar to those used for dental procedures.

In block 704, the simulation module 140 can receive image data of the patient's body (e.g., the print surface) from the base module 136. Alternatively, the simulation module 140 can receive a reference location or other identifying information to facilitate retrieval of the image data from the patient database 130. In the example of John Smith, the image data can include a series of MRI images compiled into a 3D model of his pelvis, specifically the right-side socket of the ball joint where the femur meets the pelvis.

The simulation module 140 can also query, at block 706, the procedure database 132 for data about the procedure to be performed. In the example of John Smith, the procedure to be performed can be the repair and reconstruction of the right socket of the ball joint where the femur meets the pelvis. The procedure can include instructions for reinforcing the fractured bone and rebuilding missing pieces of the socket. The procedure data can include incision locations, tool pathing, required resources including personnel and tools, etc.

The simulation module 140 can simulate, at block 708, the procedure according to the received 3D printing instructions and the procedure data retrieved from the procedure database 132. The data from the procedure database 132 may include data necessary for completion of the procedure to be simulated, which may not be included in the print instructions, such as work to access and prepare the print site prior to use of the 3D printer 118.

The simulation can include a combination of a surgical simulation and/or a 3D print simulation to determine whether the print operation can be completed using the 3D printing instructions. The simulation may verify whether the print can be completed within particular space constraints of the patient, whether the selected materials will allow for printing without a support structure, and if necessary, whether a removable support structure may be included and remain removable after the print is completed. In some implementations, as described herein, the simulation may be repeated multiple times to account for potential variations, such as movement by the patient, variable performance by the surgical robot 102 or surgeon, etc.

In block 710, the simulation module 140 can determine whether the simulated procedure is successful. The simulation can be successful if the simulation completes without identifying issues or error conditions. Examples of error conditions may include but are not limited to parts of the robotic arm 112, end effector 114, 3D printer 118, and/or other tools being unable to move as instructed by the 3D printing instructions without colliding with the patient's tissues, the nozzle 122 being unable to achieve necessary positions and orientations described by the instructions, the substrate not being properly supported resulting in a failure of the simulated print, etc.

If the simulation is successful, no issues may be identified during the simulation and the simulation module 140 can send simulation results to the base module 136 (block 714).

If the simulation is unsuccessful, one or more issues may be identified and the simulation module 140 can create an error report in block 712. For example, the nozzle 122 can be found to not have clearance necessary to deposit the substrate at approximately 35 minutes into the print inside, within, or otherwise part of the patient's body. Accordingly, in block 712, the simulation module 140 can create the error report, or log of issues identified during the simulation of the procedure. The error report may include issues such as lack of clearance for movement of the robotic arm 112, end effector 114, 3D printer 118, and/or navigation of the nozzle 122 to locations and orientations required to execute the print safely and accurately within the patient's body. Issues may additionally include print issues, such as need and ability to print removable supports and/or ability to complete the print without any temporary support structures.

The error report may be used by the planning module 138 to modify the 3D printing instructions if necessary. In the example of John Smith, an error report can indicate that the nozzle 122 does not have the clearance to be able to deposit the substrate at approximately 35 minutes into the print. This error report can be received at the planning module 138 and used to modify the 3D printing instructions accordingly. The modified instructions can then be sent back to the simulation module 140 for additional testing. If the simulation is successful, then the issue with the nozzle 122 has been resolved and the modified instructions can be used during runtime. If the simulation is still unsuccessful, the simulation module 140 can generate another error report and send back to the planning module 138 for further modifications to be made to the instructions.

In block 714, the simulation results can be sent by the simulation module 140 to the base module 136. The simulation results may include a success or failure and/or may additionally include an error report as described herein. In some implementations, the error report may be included regardless of whether the simulation was successful or unsuccessful. In some implementations, the simulation result may be successful, and an error report can be transmitted with multiple issues identified, however the issues may be advisory and may not prevent execution of the print instructions. However, the errors can indicate that modification to the 3D printing instructions can be made at the discretion of the surgeon. As described herein, the base module 136 can transmit the simulation results, such as the error report, to the planning module 138 for modifications to be made to the 3D printing instructions. The simulation results can also be transmitted to the user interface 110 of the surgeon, so that the surgeon can review and/or implement one or more modifications to the 3D printing instructions before runtime use in the patient's surgical procedure.

Figure 8:
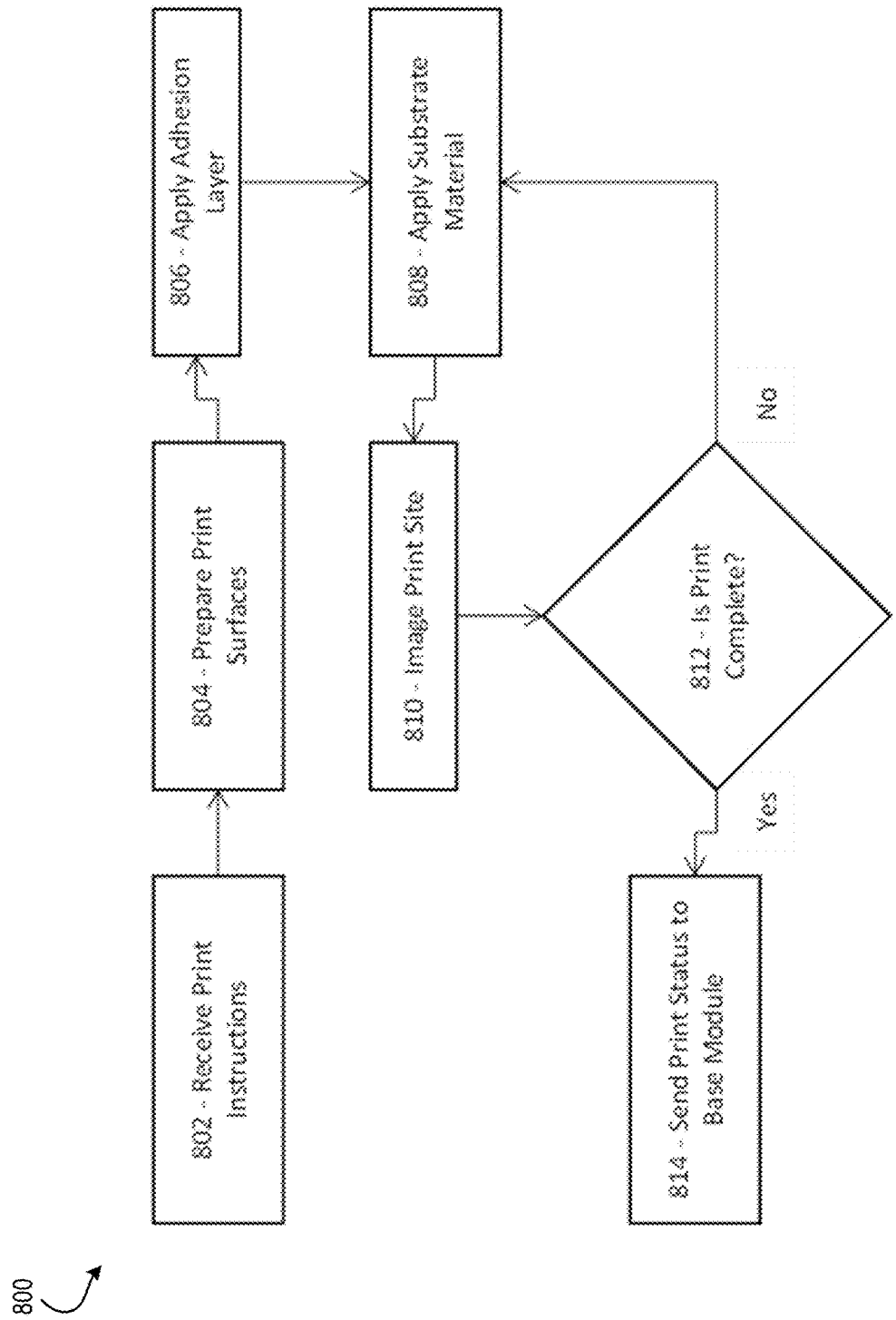
FIG. 8 is a flowchart of a process for performing the in situ 3D printing of the implant during the surgical procedure of FIG. 5.

FIG. 8 is a flowchart of a process 800 for performing the in situ 3D printing of the implant during the surgical procedure of FIG. 5. The process 800 can be performed by the print module 142. One skilled in the art will appreciate that, for this and other processes and methods disclosed herein, the functions performed in the processes and methods may be implemented in differing order. Furthermore, the outlined blocks and operations are only provided as examples, and some of the blocks and operations may be optional, combined into fewer blocks and operations, or expanded into additional blocks and operations without detracting from the essence of the disclosed technology.

The process 800 begins with the print module 142 receives, at block 802, the 3D printing instructions from the base module 136. The instructions may include the design of the structure to be printed by the 3D printer 118, which substrates 124 to use and where, which print surfaces are to be adhered to and which should remain unattached to the printed structure, etc. The instructions may additionally include tool pathing for the 3D printer 118, end effector, 114, robotic arm 112, and/or any other tools utilized during the procedure. Similarly, the print instructions may include location and orientation of the 3D printer 118, nozzle 122, and/or settings for the extruder 120. The instructions may include instructions for use of the selected at least one substrate, such as mixing a two-part resin or the temperature to which to heat a thermoplastic and the rates at which the substrate should be extruded. The instructions may further include a method of curing the printed structure and tools and resources required, such as a source of ultraviolet light.

In the example of patient John Smith, the print instructions can include a design for an implant fused to the pelvis of the patient including reconstructing the socket of the hip joint. The print instructions can include information about an adhesive layer that is made of polymethylmethacrylate bone cement and a substrate that can be a UV curable resin similar to those used for dental procedures.

In block 804, the print module 142 can generate instructions, to be executed by the controller 104 of the surgical robot 102, to prepare print surfaces to receive the substrate in the 3D printing instructions. The substrate may be the primary print material such as a UV curable resin, and/or may initially include an adhesion layer, such as polymethylmethacrylate bone cement. Preparation of the print surfaces can be dependent upon the procedure. For example, preparing a hard tissue, such as bone, to receive the substrate may include operations for removing soft tissues, cleaning, and drying the bone surface, and possibly removing some of the bone. In some implementations, the print surface may be a soft tissue. Therefore, the instructions for preparing the print surface can include removing prior tissues, such as removal of failing ligaments, if a ligament is being replaced.

As described herein, preparation of the print surfaces may be completed autonomously by the surgical robot 102, manually by a surgeon, or supervised semi-autonomous operations performed by the surgeon and the surgical robot 102. The preparation of the print surfaces may be included in the print instructions, or the print instructions may only include actions to be taken by the robotic arm 112 and 3D printer 118 to fabricate the printed structure. Therefore, the print module 142 can generate the preparation instructions and transmit to the controller 104 of the surgical robot 102 for execution during the surgical procedure.

The print site may be imaged prior to initiation of the 3D printing instructions to verify that the print surfaces and print site have been prepared according to the 3D printing instructions. For example, the print module 142 can generate instructions to one or more of the imaging devices 126A-N to image the print surfaces and/or the print site. The print module 142 can receive the images and analyze such images to determine whether the site has been prepared according to the 3D printing instructions. If the site is prepared accordingly, the print module 142 can proceed to the next block 806, described below. If the site is not prepared accordingly, the print module 142 can generate one or more additional instructions to be executed by the controller 104 of the surgical robot 102 that causes components of the surgical robot 102 to continue preparing the print site.

In block 806, the print module 142 can generate instructions for execution by the controller 104 of the surgical robot 102 to apply an adhesion layer of substrate 124, if indicated by the 3D printing instructions. The adhesion layer may use the same substrate 124 as the primary substrate 124 to be used for the main part of the printed structure. The adhesion layer may, in some implementations, be a separate substrate 124 to promote adhesion between the print surface and the substrate 124 material. In some implementations, the adhesion layer may include a material to prevent adhesion, such as if there are surfaces upon which the substrate 124 should not adhere to. Sometimes, the adhesion layer can be polymethylmethacrylate bone cement to ensure a strong bond between an internal structure of the patient and the primary substrate 124 (e.g., a UV curable resin).

The print module 142 can then generate instructions for execution by the controller 104 to apply the substrate 124 material to the print site via the 3D printer 118 using the 3D printing instructions (block 808). The instructions can require the 3D printer 118 to print layer by layer of the substrate 124 material inside, adjacent, or otherwise affixed to a portion of the patient's body. Between each layer, the print module 142 can optionally receive sensor and/or imaging data of the print site and/or the print surface, which can be analyzed by the print module 142 to determine whether the 3D printing is being performed accurately and precisely according to the 3D printing instructions. If the 3D printing is being performed accurately, the print module 142 can transmit instructions for a next layer of the substrate 124 to be injected/formed at least partially inside or otherwise within the patient. In some implementations, if the 3D printing is being performed accurately, the 3D printer 118 can continue to form subsequent layers. In some implementations, if the printing is not being performed as expected, the print module 142 can generate instructions that cause the controller 104 to halt actions performed by the 3D printer 118. The print module 142 can also transmit a notification to the user interface 110 of the surgeon, alerting the surgeon of one or more real-time issues with the 3D printing. As described herein, the surgeon can then select/implement one or more actions to be performed manually, autonomously by the surgical robot 102, and/or semi-autonomously by the surgical robot 102 in order to correct the real-time issues.

Applying the substrate 124 material in block 808 can include executing instructions that cause the substrate 124 to be extruded by the extruder 120 through the nozzle 122 of the 3D printer 118. In the example of the patient John Smith, the substrate 124 can be a UV curable resin. Application of the UV curable resin may include extruding a layer of resin alternating with a period of 15 seconds of ultraviolet light. This time period may vary depending on the properties of the resin being used and the amount of resin being cured. In some implementations, the substrate 124 material may be a clay resin, which cures after a period of working time that begins when a hardener is mixed with the clay resin. Further implementations may utilize a laser sintering process in which a metal power is applied, that may include the use of a binder material, and a laser can be used to heat and bond the applied metal powder to the layer of substrate 124 beneath it. In some implementations, thermoplastics can be used, which may be pure materials or composite materials containing other materials such as metals or reinforcing fibers.

The print module 142 can request and receive images of the print site from one or more of the imaging devices 126A-N in block 810. The imaging devices 126A-N may be a visible light camera, an Mill, or any other type of imaging device, such as CT, PET, ultrasound, etc. Multiple imaging devices 126A-N and imaging modalities may also be utilized. In the example of John Smith, both a visible light camera affixed to the end of an endoscope and an MRI to image the progress of the reconstruction of John Smith's pelvis can be received in block 810. Such imaging can be used by the print module 142 to monitor progress of the print and identify possible errors in the print, as described above.

The print module 142 can determine, at block 812, whether the 3D printing is complete. The print can be complete if the 3D printing instructions have been fully executed. The print can also be complete if the print design has been completed. In the example of John Smith, the print can be completed once the print instructions have been fully executed and John Smith's pelvis has been fully reconstructed by the 3D printer 118. Imaging data captured by the one or more imaging devices 126A-N and received in block 810 can be used by the print module 142 to determine whether the print is complete.

In some implementations, the print can be determined to be complete due to a failure of the print. The failure can be identified from the imaging data received in block 810. In some implementations, the failure of the print can also be determined from sensor data received during the procedure from one or more patient monitoring sensors and/or sensors attached to the components of the surgical robot 102 performing the 3D printing instructions. When a failure of the print is identified, 3D printing can be stopped and intervention by the surgeon may be required. Intervention can also be performed autonomously or semi-autonomously by components of the surgical robot 102. Intervention can include removing the printed substrate from inside, affixed to, adjacent, or otherwise around the patient's body to facilitate resumption or restarting of the print process. One or more other interventions can be generated and determined by the print module 142, depending on the type of failure that is identified.

If the printing is not complete (e.g., additional layers of the substrate 124 need to be put down to complete building the structure inside the patient), the print module 142 can return to block 808. Blocks 808-810 can be repeated until the print module 142 determines in block 812 that the printing is complete.

If the printing is complete, the print module 142 can send, at block 814, a print status to the base module 136. The print status can include a completion status and may additionally include success or failure status. The print status can then be outputted at the user interface 110 for presentation to the surgeon. If the print status is successfully, the base module 136 can then transmit instructions to the controller 104 that, when executed, cause the components of the surgical robot 102 to complete the procedure, such as removing the 3D printer 118 from the incision site, cleaning the incision site, closing the incision site, monitoring the patient conditions, etc. In the example of John Smith, the print can be complete and successful, so the print status can indicate that John Smith's pelvis has been fully reconstructed.

Figure 9:
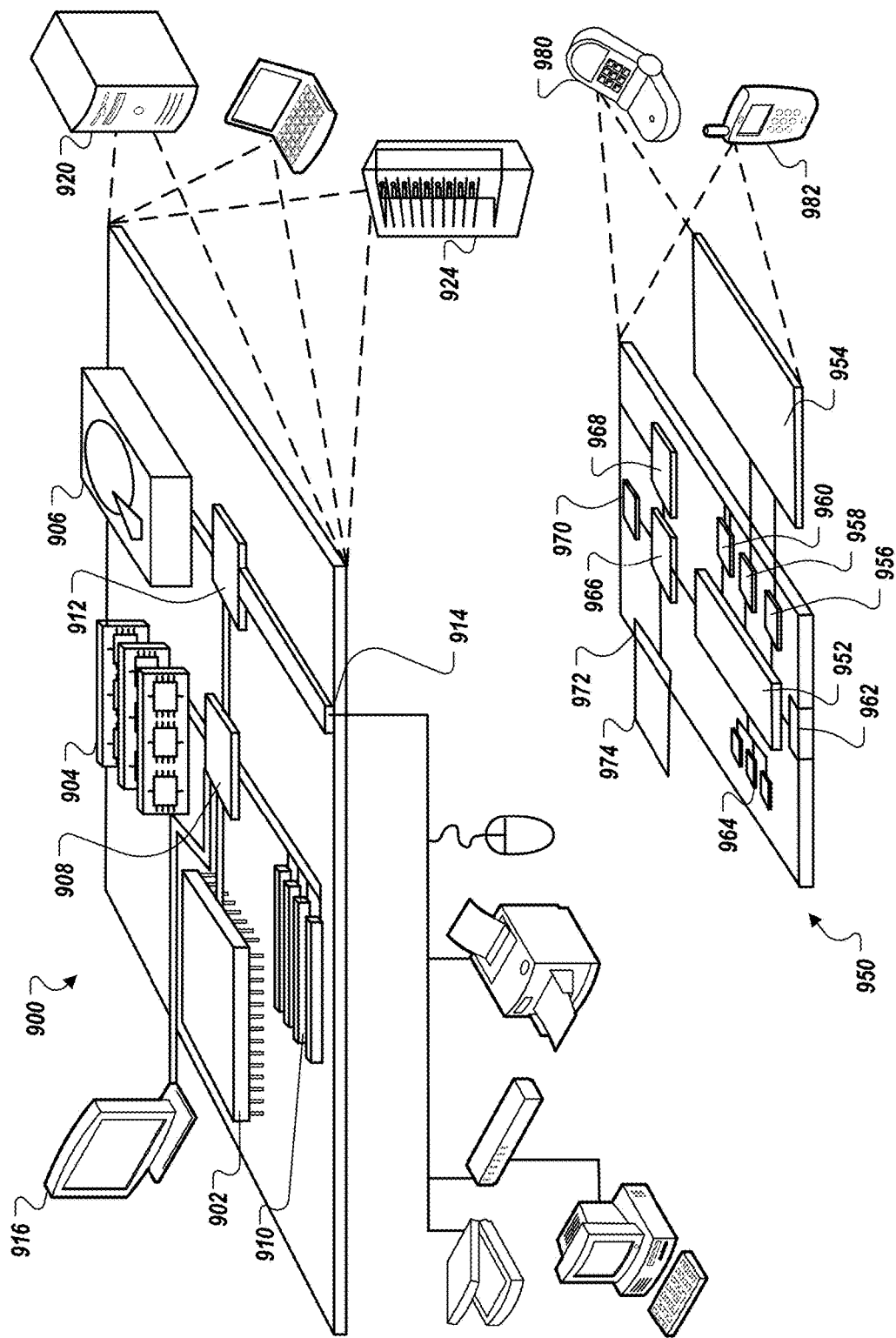
FIG. 9 is a schematic diagram that shows an example of a computing device and a mobile computing device.

FIG. 9 shows an example of a computing device 900 and an example of a mobile computing device that can be used to implement the techniques described here. The computing device 900 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 900 includes a processor 902, a memory 904, a storage device 906, a high-speed interface 908 connecting to the memory 904 and multiple high-speed expansion ports 910, and a low-speed interface 912 connecting to a low-speed expansion port 914 and the storage device 906. Each of the processor 902, the memory 904, the storage device 906, the high-speed interface 908, the high-speed expansion ports 910, and the low-speed interface 912, are interconnected using various busses, and can be mounted on a common motherboard or in other manners as appropriate. The processor 902 can process instructions for execution within the computing device 900, including instructions stored in the memory 904 or on the storage device 906 to display graphical information for a GUI on an external input/output device, such as a display 916 coupled to the high-speed interface 908. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 904 stores information within the computing device 900. In some implementations, the memory 904 is a volatile memory unit or units. In some implementations, the memory 904 is a non-volatile memory unit or units. The memory 904 can also be another form of computer-readable medium, such as a magnetic or optical disk.

The storage device 906 is capable of providing mass storage for the computing device 900. In some implementations, the storage device 906 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 904, the storage device 906, or memory on the processor 902.

The high-speed interface 908 manages bandwidth-intensive operations for the computing device 900, while the low-speed interface 912 manages lower bandwidth-intensive operations. Such allocation of functions is exemplary only. In some implementations, the high-speed interface 908 is coupled to the memory 904, the display 916 (e.g., through a graphics processor or accelerator), and to the high-speed expansion ports 910, which can accept various expansion cards (not shown). In the implementation, the low-speed interface 912 is coupled to the storage device 906 and the low-speed expansion port 914. The low-speed expansion port 914, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 900 can be implemented in a number of different forms, as shown in the figure. For example, it can be implemented as a standard server 920, or multiple times in a group of such servers. In addition, it can be implemented in a personal computer such as a laptop computer 922. It can also be implemented as part of a rack server system 924. Alternatively, components from the computing device 900 can be combined with other components in a mobile device (not shown), such as a mobile computing device 950. Each of such devices can contain one or more of the computing device 900 and the mobile computing device 950, and an entire system can be made up of multiple computing devices communicating with each other.

The mobile computing device 950 includes a processor 952, a memory 964, an input/output device such as a display 954, a communication interface 966, and a transceiver 968, among other components. The mobile computing device 950 can also be provided with a storage device, such as a micro-drive or other device, to provide additional storage. Each of the processor 952, the memory 964, the display 954, the communication interface 966, and the transceiver 968, are interconnected using various buses, and several of the components can be mounted on a common motherboard or in other manners as appropriate.

The processor 952 can execute instructions within the mobile computing device 950, including instructions stored in the memory 964. The processor 952 can be implemented as a chipset of chips that include separate and multiple analog and digital processors. The processor 952 can provide, for example, for coordination of the other components of the mobile computing device 950, such as control of user interfaces, applications run by the mobile computing device 950, and wireless communication by the mobile computing device 950.

The processor 952 can communicate with a user through a control interface 958 and a display interface 956 coupled to the display 954. The display 954 can be, for example, a TFT (Thin-Film-Transistor Liquid Crystal Display) display or an OLED (Organic Light Emitting Diode) display, or other appropriate display technology. The display interface 956 can comprise appropriate circuitry for driving the display 954 to present graphical and other information to a user. The control interface 958 can receive commands from a user and convert them for submission to the processor 952. In addition, an external interface 962 can provide communication with the processor 952, so as to enable near area communication of the mobile computing device 950 with other devices. The external interface 962 can provide, for example, for wired communication in some implementations, or for wireless communication in other implementations, and multiple interfaces can also be used.

The memory 964 stores information within the mobile computing device 950. The memory 964 can be implemented as one or more of a computer-readable medium or media, a volatile memory unit or units, or a non-volatile memory unit or units. An expansion memory 974 can also be provided and connected to the mobile computing device 950 through an expansion interface 972, which can include, for example, a SIMM (Single In Line Memory Module) card interface. The expansion memory 974 can provide extra storage space for the mobile computing device 950, or can also store applications or other information for the mobile computing device 950. Specifically, the expansion memory 974 can include instructions to carry out or supplement the processes described above, and can include secure information also. Thus, for example, the expansion memory 974 can be provide as a security module for the mobile computing device 950, and can be programmed with instructions that permit secure use of the mobile computing device 950. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 964, the expansion memory 974, or memory on the processor 952. In some implementations, the computer program product can be received in a propagated signal, for example, over the transceiver 968 or the external interface 962.

The mobile computing device 950 can communicate wirelessly through the communication interface 966, which can include digital signal processing circuitry where necessary. The communication interface 966 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 968 using a radio-frequency. In addition, short-range communication can occur, such as using a Bluetooth, WiFi, or other such transceiver (not shown). In addition, a GPS (Global Positioning System) receiver module 970 can provide additional navigation- and location-related wireless data to the mobile computing device 950, which can be used as appropriate by applications running on the mobile computing device 950.

The mobile computing device 950 can also communicate audibly using an audio codec 960, which can receive spoken information from a user and convert it to usable digital information. The audio codec 960 can likewise generate audible sound for a user, such as through a speaker, e.g., in a handset of the mobile computing device 950. Such sound can include sound from voice telephone calls, can include recorded sound (e.g., voice messages, music files, etc.) and can also include sound generated by applications operating on the mobile computing device 950.

The mobile computing device 950 can be implemented in a number of different forms, as shown in the figure. For example, it can be implemented as a cellular telephone 980. It can also be implemented as part of a smart-phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method for printing a structure in situ within a patient's body, the method comprising:
receiving, by a computer system, image data of a print site at least partially within the patient's body, wherein the print site represents a location at least partially inside the patient's body where the structure is to be printed;
identifying, by the computer system and based on the received image data, a print surface of the print site at least partially within the patient's body;
generating, by the computer system, printing instructions for printing the structure on the identified print surface of the print site at least partially within the patient's body, including:
(i) simulating, by the computer system and using the received image data, the printing instructions to verify successful printing of the structure on the identified print surface of the print site at least partially within the patient's body;
(ii) determining, by the computer system, whether a result of simulating the printing instructions indicates successful printing of the structure on the identified print surface of the print site at least partially within the patient's body; and
(iii) generating, by the computer system and based on a determination that the result of simulating the printing instructions indicates successful printing, the printing instructions to be executed by a controller of a surgical robot comprising a printing device; and
controlling, by the computer system and using the printing instructions, the printing device to physically print the structure on the identified print surface of the print site at least partially within the patient's body.

2. The method of claim 1, wherein the printing device is a 3D printer.

3. The method of claim 1, wherein the printing device is an additive manufacturing device.

4. The method of claim 1, wherein the structure is an implant.

5. The method of claim 1, wherein the receiving of the image data is performed by a base module of the computer system.

6. The method of claim 1, wherein the generating of the printing instructions is performed by a planning module of the computer system.

7. The method of claim 1, wherein the simulating of the printing instructions is performed by a simulation module of the computer system.

8. The method of claim 1, wherein the generating, based on the determination that the result of simulating the printing instructions indicates successful printing of the structure on the identified print surface of the print site at least partially within the patient's body, the printing instructions is performed by a print module of the computer system.

9. A method for printing a structure in situ within a patient's body, the method comprising:
receiving, by a computer system, image data of a print site at least partially within the patient's body, wherein the print site represents a location at least partially inside the patient's body where the structure is to be printed;
identifying, by the computer system and based on the received image data, a print surface of the print site at least partially within the patient's body;
generating system, printing instructions for printing the structure on the identified print surface of the print site at least partially within the patient's body, including:
(i) retrieving procedure data for a surgical procedure to be performed to print the structure at the print site at least partially within the patient's body;
(ii) generating, based on the identified print surface and the retrieved procedure data, a print design for the structure to be printed on the identified print surface of the print site at least partially within the patient's body;
(iii) retrieving substrate material data for substrate materials to be used in printing the structure according to the print design; and
(iv) selecting at least one of the substrate materials based on respective substrate material data satisfying printing criteria; and
controlling, by the computer system and using the printing instructions, a printing device to physically print the structure on the identified print surface of the print site at least partially within the patient's body.

10. The method of claim 1, further comprising:
generating based on a determination that the result of simulating the printing instructions indicates unsuccessful printing, an error report including indications of issues during simulated execution of one or more of the printing instructions;
modifying, by the computer based on the error report, the printing instructions; and
simulating system, the modified printing instructions to verify successful printing of the structure on the identified print surface of the print site at least partially within the patient's body.

11. The method of claim 1, wherein the controlling, by the computer system, of the printing device to physically print the structure comprises:
generating instructions, based on the printing instructions, executed by the printing device to apply a substrate material to a prepared print surface;
continuously receiving, from at least one imaging device, image data of the print surface as the print surface is prepared and the substrate material is applied to the prepared print surface;
determining, based on the received image data, whether the structure is being printed by the printing device according to the printing instructions; and
returning, based on a determination that the structure is being printed according to the printing instructions, an indication that the structure is printed at least partially inside the patient's body during a surgical procedure.

12. The method of claim 11, further comprising: generating second instructions, based on the printing instructions, executable by the printing device to apply an adhesion layer to the prepared print surface before applying the substrate material.

13. The method of claim 11, further comprising:
generating second instructions, based on a determination that the structure is not printed according to the printing instructions, executable by the printing device to stop printing the structure at least partially inside the patient's body; and
transmitting the instructions to the printing device for execution during the surgical procedure.

14. The method of claim 11, wherein the printing instructions include instructions that cause the printing device to prepare the print surface, the instructions comprising at least one of (i) removing soft tissue near the print surface within the patient's body, (ii) cleaning a bone surface within the patient's body that is part of the print surface, (iii) drying the bone surface within the patient's body that is part of the print surface, (iv) removing a portion of the bone surface, and (v) removing failing internal structures of the patient's body to be replaced by the structure.

15. The method of claim 11, wherein the generating instructions, based on the printing instructions, executed by the printing device to apply the substrate material to the prepared print surface comprises:
    drawing, by an extruder of the printing device, the substrate material from a supply; and
    depositing, by the extruder via a nozzle of the printing device, a predetermined amount of the drawn substrate material onto the prepared print surface,
    wherein the extruder is set to a predetermined position and a predetermined orientation defined by the printing instructions.

16. The method of claim 1, wherein the printing instructions include at least one of (i) a design of the structure to be printed on the print surface at least partially inside the patient's body, (ii) at least one substrate material to use for printing the structure, (iii) a location on the print surface to print the structure with the at least one substrate material, (iv) an indication of at least a portion of the print surface that should remain unattached to the structure, (v) tool pathing for the printing device to print the structure on the print surface, (vi) location and orientation information for the printing structure to print the structure on the print surface, and (vii) instructions for extruding the at least one substrate material on the print surface.

17. One or more non-transitory computer-readable media having instructions stored thereon executed by one or more processors, cause performance of operations comprising:
    receiving image data of a print site at least partially within a patient's body, wherein the print site represents a location at least partially inside the patient's body where a structure is to be printed;
    identifying, based on the received image data, a print surface of the print site at least partially within the patient's body;
    generating printing instructions for printing the structure on the identified print surface of the print site at least partially within the patient's body, including:
        (i) simulating, using the received image data, the printing instructions to verify successful printing of the structure on the identified print surface of the print site at least partially within the patient's body;
        (ii) determining whether a result of simulating the printing instructions indicates successful printing of the structure on the identified print surface of the print site at least partially within the patient's body; and
        (iii) generating, based on a determination that the result of simulating the printing instructions indicates successful printing, the printing instructions to be executed by a controller of a surgical robot comprising a printing device; and
    controlling the printing device to physically print the structure on the identified print surface of the print site at least partially within the patient's body using the printing instructions.

18. The one or more non-transitory computer-readable media of claim 17, wherein the printing device is a 3D printer.

19. The one or more non-transitory computer-readable media of claim 17, wherein the printing device is an additive manufacturing device.

20. The one or more non-transitory computer-readable media of claim 17, wherein the structure is an implant.

21. The one or more non-transitory computer-readable media of claim 17, wherein receiving the image data is performed by a base module of a computer system.

22. A system, comprising:
    one or more processors; and
    one or more non-transitory computer-readable media having instructions stored thereon executed by the one or more processors, cause the one or more processors to perform operations comprising:
        receiving image data of a print site at least partially within a patient's body, wherein the print site represents a location at least partially inside the patient's body where a structure is to be printed;
        identifying, based on the received image data, a print surface of the print site at least partially within the patient's body;
        generating printing instructions for printing the structure on the identified print surface of the print site at least partially within the patient's body, including:
            (i) simulating, using the received image data, the printing instructions to verify successful printing of the structure on the identified print surface of the print site at least partially within the patient's body;
            (ii) determining whether a result of simulating the printing instructions indicates successful printing of the structure on the identified print surface of the print site at least partially within the patient's body; and
            (iii) generating, based on a determination that the result of simulating the printing instructions indicates successful printing, the printing instructions to be executed by a controller of a surgical robot comprising a printing device; and
        controlling the printing device to physically print the structure on the identified print surface of the print site at least partially within the patient's body using the printing instructions.

23. The system of claim 22, wherein the printing device is a 3D printer.

24. The system of claim 22, wherein the printing device is an additive manufacturing device.

25. The system of claim 22, wherein the structure is an implant.

26. The system of claim 22, wherein receiving the image data is performed by a base module of the system.

* * * * *